United States Patent
Lum et al.

(10) Patent No.: US 9,499,619 B2
(45) Date of Patent: Nov. 22, 2016

(54) POLYCLONAL BISPECIFIC ANTIBODY COMPOSITIONS AND METHOD OF USE

(71) Applicants: TransTarget, Inc., Burlingame, CA (US); Wayne State University, Detroit, MI (US)

(72) Inventors: Lawrence G. Lum, Harrison Township, MI (US); Manley Huang, Palo Alto, CA (US)

(73) Assignees: TRANSTARGET, INC., Burlingame, CA (US); WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/637,194

(22) Filed: Mar. 3, 2015

(65) Prior Publication Data

US 2015/0175700 A1    Jun. 25, 2015

Related U.S. Application Data

(62) Division of application No. 13/508,182, filed as application No. PCT/US2010/055707 on Nov. 5, 2010, now Pat. No. 8,999,398.

(60) Provisional application No. 61/259,019, filed on Nov. 6, 2009.

(51) Int. Cl.
| | |
|---|---|
| *C07K 16/00* | (2006.01) |
| *C07K 16/28* | (2006.01) |
| *C07K 16/06* | (2006.01) |
| *C07K 16/08* | (2006.01) |
| *C07K 16/10* | (2006.01) |
| *A61K 35/17* | (2015.01) |
| *A61K 39/42* | (2006.01) |
| *C12N 5/0783* | (2010.01) |
| *A61K 39/00* | (2006.01) |

(52) U.S. Cl.
CPC ........... *C07K 16/2809* (2013.01); *A61K 35/17* (2013.01); *A61K 39/42* (2013.01); *C07K 16/06* (2013.01); *C07K 16/082* (2013.01); *C07K 16/084* (2013.01); *C07K 16/087* (2013.01); *C07K 16/088* (2013.01); *C07K 16/109* (2013.01); *C12N 5/0638* (2013.01); *A61K 2039/505* (2013.01); *C07K 2317/31* (2013.01); *C12N 2501/2302* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 7,763,243 | B2 | 7/2010 | Lum et al. |
| 2003/0185823 | A1 | 10/2003 | Lum et al. |
| 2004/0234521 | A1 | 11/2004 | Himawan |
| 2006/0034767 | A1 | 2/2006 | Lum et al. |
| 2006/0210564 | A1 | 9/2006 | Kumagai et al. |
| 2007/0190063 | A1 | 8/2007 | Bahjat et al. |
| 2008/0187545 | A1 | 8/2008 | Shenk et al. |

OTHER PUBLICATIONS

International Search Report from PCT/US2010/055707, dated Jan. 7, 2011.

*Primary Examiner* — Michail Belyavskyi
(74) *Attorney, Agent, or Firm* — Kilpatrick Townsend & Stockton LLP

(57) ABSTRACT

The invention relates to compositions and methods for treating a host infected with a pathogen. The composition comprising a population of polyclonal bispecific binding molecules that can target and eliminate a host cell infected with the pathogen. Methods for activating and arming cytotoxic immune cells with the composition for use in treating a patient infected with a pathogen are also provided.

28 Claims, 4 Drawing Sheets

POLYCLONAL BISPECIFIC ANTIBODY COMPOSITIONS AND METHOD OF USE

CROSS-REFERENCES TO RELATED APPLICATIONS

This application is a divisional of U.S. application Ser. No. 13/508,182, filed Jul. 16, 2012, as the US National Stage of International Appl. No. PCT/US2010/055707, filed Nov. 5, 2010, which claims priority to U.S. Provisional Appl. No. 61/259,019, filed Nov. 6, 2009, the disclosures of each are incorporated herein in their entirety.

BACKGROUND OF THE INVENTION

The infection of a patient with a pathogen remains a frequent, costly, and serious problem in health care despite advances in medical technology. For example, reactivation or infection with human viruses such as Cytomegalovirus (CMV), Epstein-Barr virus (EBV), Herpes simplex virus (HSV), Hepatitis viruses A, B, and C, and BK virus (BKV) markedly limit the success of organ and/or allogeneic stem cell transplantation (alloSCT). Taking the example of CMV, infection and disease results in life threatening complications following alloSCT and/or organ transplantation, even with appropriate use of anti-viral agents. Reactivation of CMV is associated with and augments acute graft-versus-host disease (GvHD) and organ rejection. Treatment of GvHD with immunosuppression enhances the cycle of further CMV reactivation. None of the current strategies are completely effective in preventing or treating CMV infections after transplantation.

Immunotherapy has been studied as an alternative strategy to treat CMV disease post-alloSCT. Polyclonal intravenous immunoglobulin (IVIG) and CMV-specific IVIG (Cytogam®) have been used with little success. Himawan (US Pre-Grant Pub. No. 2004/0234521) has studied the use of a polyclonal antibody directed against a pathogen conjugated to an anti-c3b antibody as a means for clearing pathogen from the circulation. This approach, while demonstrating limited success in exploiting the complement system to clear free floating pathogen from the circulation does not address the issue of treating cells infected with the pathogen.

Immunotherapy with CMV-specific donor-derived or engineered cytotoxic T-lymphocytes (CTL) has been tried since 1990s, but is yet to be translated to routine clinical use. For example, post-alloSCT infusions of cloned donor CMV-specific cytotoxic T lymphocytes (CTL) are dose-limiting, time-restricted, expensive, labor intensive, and have yet to produce any meaningful anti-CMV T cell response in immunocompromised hosts. See, Walter et. al., *NEJM.* 1995.

Previous studies in the field of cancer therapy have indicated that activated T-cells (ATC) can be redirected to tumor cells using bispecific antibodies against various malignancies. For example, armed ATC directed at Her2/neu, EGFR, CD20, and CD33 have been used to target prostate, lung, pancreas, head and neck, and ovarian cancer as well as multiple myeloma, non-Hodgkin's lymphoma, and acute myelogenous leukemia. See, e.g. Davol, et al., *Clin Prostate Cancer* 2004; Reusch, et al., *Clin Cancer Res.* 2006; Chan, et al., *Clin Cancer Res.* 2006. Similar attempts for targeting virally infected cells have met with limited success due to the difficulty in identifying or generating an antibody against an antigen of the pathogen that is expressed on the surface of an infected cell and is not subject to antigenic drift. See, e.g., Moran, et al., (1991) *J. Immunol.* 146(1):321-326; Fernandez-Sesma, et al. (1996) *J. Virol.* 70(7):4800-4804; and Fernandez-Sesma, et al., (1998) *J. Immunol.* 160:1841-1849.

Thus, there is a need for an effective, safe non-toxic therapy for treating patients suffering pathogenic infection or reactivation. The instant invention addresses this and other needs by providing for novel compositions and methods that dramatically improve the treatment and management of patients infected with a pathogen.

BRIEF SUMMARY OF THE INVENTION

The invention provides for a composition comprising a population of polyclonal bispecific binding molecules. Each bispecific binding molecule of the population comprises a first antigen binding moiety that specifically binds to an antigen expressed on the surface of a cytotoxic immune cell, fused to a second antigen binding moiety that binds to an antigen of a pathogen expressed on the surface of a cell infected with the pathogen. The population of the bispecific binding molecules is polyclonal with respect to the second antigen binding moieties, which comprise a heterogeneous population of binding moieties directed against the pathogen.

In some embodiments of the invention, the cytotoxic immune cell is an activated T-cell (ATC), or a natural killer (NK) cell, monocyte, macrophage, or a dendritic cell. In some embodiments, the composition comprises more than one type of first antigen binding moiety wherein each of the first antigen binding moieties specifically binds to an antigen expressed on a different cytotoxic immune cell. In some embodiments, the first antigen binding moiety is a polyclonal antibody. In some embodiments, the first antigen binding moiety is an anti-cytotoxic immune cell polyclonal antisera. In some embodiments, the first antigen binding moiety is horse anti-thymocyte globulin, or rabbit anti-thymocyte globulin. In some embodiments, the cytotoxic immune cell is derived from an autologous donor. In some embodiments the cytotoxic immune cell is derived from an allogeneic donor or pool of allogeneic donors. In some embodiments the cytotoxic immune cell is derived from a syngeneic donor.

In some embodiments, the first antigen binding moiety binds to an antigen selected from the group consisting of CD2, CD3, CD4, CD5, CD8, CD11b, CD14, CD16a, CD28, CD45, CD56 and an Fc receptor. In some embodiments the first antigen binding moiety binds to CD3. In some embodiments the first antigen binding moiety is OKT3, a functionally equivalent monoclonal antibody, or antigen-binding fragment thereof. The first antigen binding moiety can also be a polyclonal antibody or antigen binding fragment thereof with functional equivalence to OKT3. In some embodiments, the first antigen binding moiety binds to an Fc receptor.

In some embodiments, the first antigen binding moiety and the second antigen binding moiety are antibodies or antigen binding fragments thereof. In some embodiments, only the first antigen binding moiety is an antibody or antigen binding fragment thereof. In some embodiments, only the second antigen binding moiety is an antibody or an antigen binding fragment thereof. In some embodiments, the first antigen binding moiety is a monoclonal antibody or antigen binding fragment thereof and the second antigen binding moiety is a polyclonal antibody or antigen binding fragment thereof. The first and second antigen binding moieties can also be natural ligands, mimetics, proteins, or other targeting moieties that specifically bind to the desired first or second antigen.

In some embodiments, the population of polyclonal bispecific binding molecules comprises at least two different antibodies or antigen binding fragments thereof as second antigen binding moieties, with each antibody (or fragment) having a different antigen recognition specificity. In some embodiments, the antigen binding moieties are directed to different epitopes on an antigen of the pathogen. In some embodiments, at least two of the second antigen binding moieties bind to two different antigens of the pathogen, or different epitopes of an antigen of the pathogen, or bind with different affinities to an antigen, or an epitope of an antigen, of the pathogen.

In some embodiments, the population of polyclonal antibodies used as the second antigen binding moieties is derived from an immunoglobulin (Ig) enriched serum fraction. In some embodiments the Ig fraction is depleted of antibodies that recognize human leukocyte antigen molecules. In some embodiments, the polyclonal antibody (or antigen binding fragment thereof) used as the second antigen binding moiety is derived from an autologous donor. In some embodiments, the second antigen binding moiety is derived from an allogeneic donor or pool of allogeneic donors. In some embodiments, the second antigen binding moiety is derived from a syngeneic donor. In some embodiments, the second antigen binding moiety is derived from an intravenous immunoglobulin blood product (IVIG). In some embodiments the second antigen binding moiety is derived from a pooled enriched Ig preparation, that is further enriched for pathogen binding (e.g., Cytogam for CMV, Hepagam for Hepatitis).

In some embodiments, the second antigen binding moiety is derived from a host infected with or immunized against the pathogen. In some embodiments, the pathogen is an infectious agent. In some embodiments, the pathogen is a virus, a bacterium, a fungus, or a parasite. In some embodiments the pathogen is selected from cytomegalovirus (CMV), hepatitis A virus (HAV), hepatitis virus type B (HBV), hepatitis virus type C (HCV), Epstein-Barr virus (EBV), BK virus (BKV), herpes simplex virus (HSV), human immunodeficiency virus (HIV), or human papilloma virus (HPV). In some embodiments the pathogen is *Pneumocystis carinii* or *aspergillus*. In some embodiments the pathogen is CMV.

In some embodiments the activated cytotoxic immune cell (e.g., activated T cell) is armed with a population of polyclonal bispecific binding molecules. In some embodiments, the arming dose of the population of polyclonal bispecific binding molecules is in the range of 0.001 ng to 50 ng per $10^6$ cytotoxic immune cells. In some embodiments, the arming dose of the population of polyclonal bispecific binding molecules is in the range of 0.01 ng to 5 ng per $10^6$ activated cytotoxic immune cells. In some embodiments, the arming dose of the population of polyclonal bispecific binding molecules is in the range of 0.1 ng to 1 ng per $10^6$ activated cytotoxic immune cells. In some embodiments, the arming dose of the population of polyclonal bispecific binding molecules is 1 ng to 10 ng per $10^6$ cytotoxic immune cells. In some embodiments, the arming dose of the population of polyclonal bispecific binding molecules is 1 ng to 50 per $10^6$ cytotoxic immune cells. In some embodiments, the arming dose of the population of polyclonal bispecific binding molecules is 1 ng to 100 per $10^6$ cytotoxic immune cells. In some embodiments, the arming dose of the population of polyclonal bispecific binding molecules is 10 ng to 100 ng per $10^6$ cytotoxic immune cells.

Another aspect of the invention provides for a method of treating a patient infected with a pathogen. The method comprises obtaining and isolating cytotoxic immune cells from a donor(s), activating the one or more cytotoxic immune cells, expanding the cells ex vivo, arming the cells with a population of polyclonal bispecific binding molecules of the invention, and administering the armed cytotoxic immune cells to a patient in need thereof. In some embodiments, the donor is the patient (autologous). In some embodiments, the donor is allogeneic or syngeneic to the patient. In some embodiments, the donors comprise a pool of allogeneic or syngeneic donors. In some embodiments, the patient has a chronic infection. In some embodiments, the patient has received stem cell therapy (SCT). In some embodiments, the patient is suffering reactivation of a pathogen, e.g., symptomatic infection.

In some embodiments, the cytotoxic immune cells are T-cells are activated by stimulation with an anti-CD3 antibody. In some embodiments T-cells are activated by co-stimulation with anti-CD3 and anti-CD28 antibody. In some embodiments the activated T-cells are cultured in the presence of 10 IU/ml to 500 IU/ml IL-2 for 4-14 days in medium equivalent to RPMI 1640 containing at least 2% human serum or equivalent or better. In some embodiments, the activated T-cells are cultured in expansion medium in the presence of 25-100 ng/ml IL-7. In some embodiments, the activated T-cells are cultured in the presence of IL-2 and/or IL-7, as well as 25-100 ng/ml IL-15. In some embodiments, the activated T-cells are cultured in the presence of IL-7 (15-100 ng/ml) and IL-15 (25-100 ng/ml). The cells can be expanded in any combination of IL-2, IL-7, and/or IL-15, as well as recombinant cytokines and non-naturally occurring recombinant cytokines that act to expand activated T cells. For example, IL-2 can be used alone, or in combination with IL-7 and/or IL-15. Similarly, IL-7 can be used alone, or in combination with IL-2 and/or IL-15.

Each aspects of the invention as disclosed herein can be combined with any one or more, or all of the different embodiments of the invention as disclosed herein and described in more detail below.

DETAILED DESCRIPTION OF THE INVENTION

Figure 1:
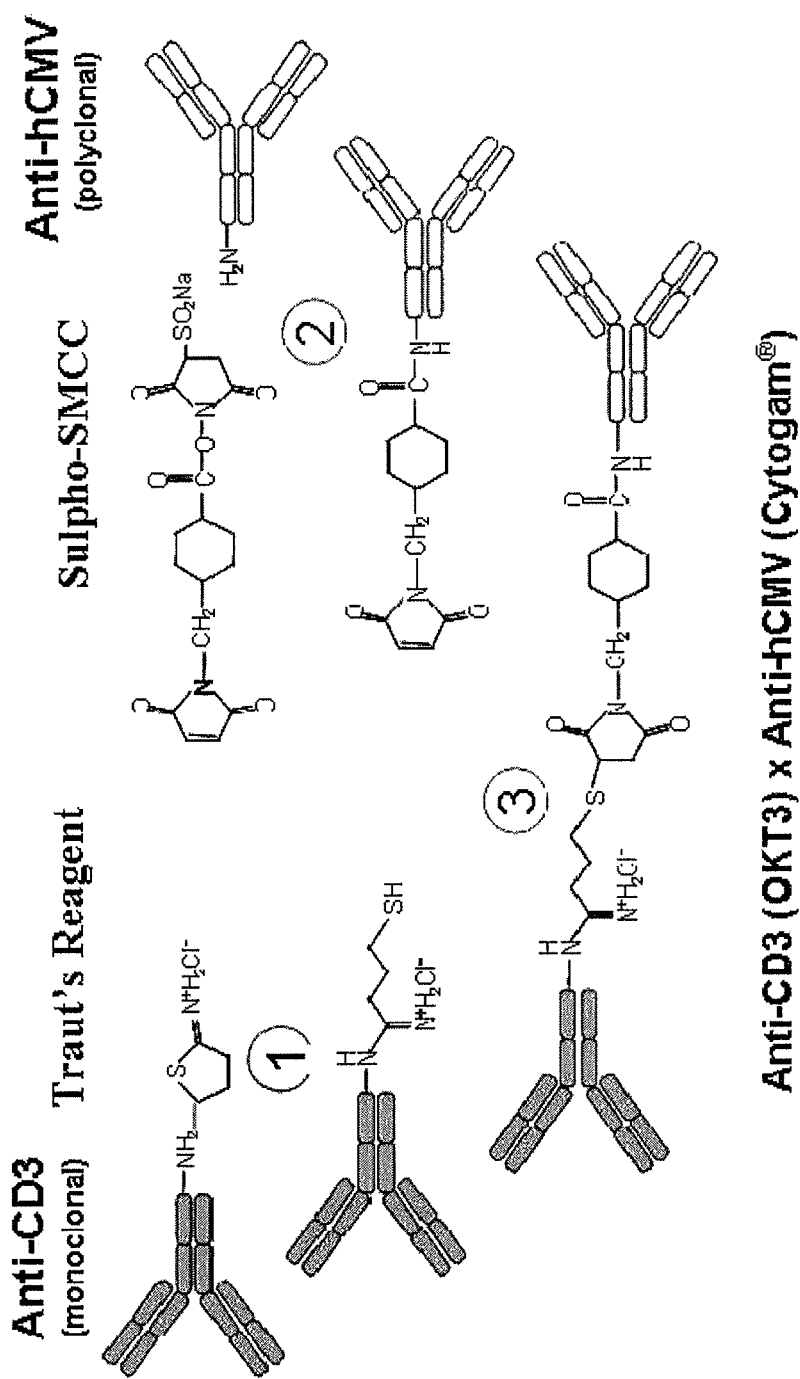
FIG. 1 shows a method for chemical heterconjugation of OKT3 (monoclonal anti-CD3) with Cytogam® (polyclonal anti-CMV) to produce the bispecific binding molecules of the invention. 1) Cross linking of anti-CD3 to Traut's reagent; 2) Cross linking of Cytogam® to Sulpho-SMCC; and 3) Heteroconjugation of anti-CD3 with Cytogam®. The procedure is detailed in Sen M et al, *J. Hemato. Stem Cell Res.* (2001).

During pathogen infection or reactivation, several antigenic targets are expressed on the surface of infected cells. Many viral pathogens, e.g., CMV, escape immune detection through a multitude of mechanisms. For example, the virus acts to downregulate MHC class I molecules to avoid T cell mediated cytotoxicity. In addition, viruses mutate quickly, resulting in multiple and changing antigens. The present invention is independent of the MHCI restriction and provides compositions and methods to overcome immune system escape by viruses and other pathogens. The invention uses cytotoxic immune cells (e.g., activated T cells) armed with a population of polyclonal bispecific binding molecules to redirect the armed cytotoxic immune cell to the desired target, e.g., through multiple epitopes or antigens on the target. The polyclonal bispecific antibody-armed effector cells eliminate infected cells expressing an antigen of the pathogen on their surface.

The present inventors have further surprisingly discovered that the concentration of the polyclonal bispecific antibody needed to arm the cytotoxic immune cells and achieve a therapeutically effective result is orders of magnitude less than the concentration of other products in the art used for treating infected patients. A reduced dose of armed cytotoxic immune cells can be given, and reduce the likelihood of graft vs host disease (GVHD) in the event the cytotoxic immune cells are allogeneic with respect to the recipient. These and other aspects of the invention are disclosed herein.

I. DEFINITIONS

As used herein the term "population of polyclonal bispecific binding molecules" refers to a plurality of bispecific binding molecules wherein each bispecific binding molecule of the population comprises two distinct antigen binding moieties fused to each other. The first antigen binding moiety specifically binds to an antigen expressed on a cytotoxic immune cell. The second antigen binding moiety binds to an antigen of a pathogen that is expressed on the surface of a cell infected with the pathogen. The population of bispecific binding molecules is polyclonal with respect to the second antigen binding moiety, rendering the population of bispecific binding molecules heterogeneous. The different members of the population are heterogeneous with respect to the second antigen binding moieties, and can bind to different antigens of a pathogen, different epitopes of an antigen of the pathogen, or different affinities to the antigen of the pathogen. Different as used herein refers to members that are structurally and distinctly different as opposed to members that are the same. The population of polyclonal bispecific binding molecules comprises at least 2 different second antigen binding moieties. In some embodiments, the first antigen binding moieties within the population are also heterogenous, e.g., directed to different cytotoxic immune cells, or different antigens on the cytotoxic immune cells (effector cells).

The term "bispecific binding molecule" as used herein refers to a single member of the population of polyclonal bispecific binding molecules. Each bispecific binding molecule is comprised of two distinct antigen binding moieties fused to each other, where the first antigen binding moiety specifically binds to an antigen expressed on a cytotoxic immune cell. The second antigen binding moiety binds to an antigen of a pathogen that is expressed on the surface of a cell infected with the pathogen.

As used herein the term "first antigen binding moiety" refers to a molecule that specifically binds to an antigen expressed on the surface of a cytotoxic immune cell, that is fused to a second antigen binding component to make the bispecific binding molecule of the invention. Exemplary non-limiting molecules that are suitable for use as first antigen binding components include antibodies and antigen binding fragments thereof, modified antibodies, and antibody mimetics. The first antigen binding moiety can have polyclonal components that include antibodies, antigen binding fragments thereof, modified antibodies, and antibody mimetics.

As used herein the term "cytotoxic immune cell" refers to a cell of the immune system that, when activated and armed with a population of polyclonal bispecific binding molecules of the invention, will target and kill cells infected with a pathogen expressing an antigen of the pathogen on their surface. Exemplary cytotoxic immune cells include, but are not limited to activated T-cells, monocytes, natural killer (NK) cells, macrophages, and dendritic cells.

As used herein the term "specifically binds" or "specific binding" means at least a 2-fold increase in binding over background, and preferably at least a 100-fold increase or greater over that of background. Specific binding between a first antigen binding moiety and an antigen expressed on the surface of a cytotoxic immune cell, e.g. a T-cell, generally means an affinity of $10^6$ $M^{-1}$ or stronger, preferable at least $10^8$ $M^{-1}$ or stronger.

As used herein the term "second antigen binding moiety" refers to an antibody or antigen binding fragment thereof that binds to an antigen of a pathogen expressed on the surface of a cell infected with the pathogen. The second antigen binding moiety when fused to the first antigen binding moiety comprises a bispecific binding molecule of the invention. In the context of the population of polyclonal bispecific binding molecules the second antigen binding moiety is a member of a heterogeneous polyclonal population of second antigen binding moieties against pathogenic antigens expressed or presented on the surface of cells infected with the pathogen.

As used herein the phrase "heterogeneous polyclonal population of antigen binding moieties," with respect to the pathogen-specific antigen binding moieties, refers to the collection of different, heterogeneous second antigen binding moieties having different complementarity determining regions (CDRs), wherein at least two of the second antigen binding moieties bind to two different antigens of the pathogen, different epitopes of an antigen of the pathogen, or with different affinities to the antigen of the pathogen. The heterogeneous polyclonal population of second antigen binding moieties can be derived from polyclonal antisera generated from a host animal, typically a human. In some embodiments, the polyclonal antisera is pooled from more than one host. In some embodiments, the host(s) are either immunized or infected with the pathogen. The heterogeneous population of second antigen binding moieties can also be derived from a library of antibodies against a pathogen, such as a phage display library.

As used herein the terms "fused," "linked" and "conjugated" refer to the linkage between the first antigen binding moiety and the second antigen binding moiety in the bispecific binding molecule. The linkage may be introduced through either recombinant (e.g. recombinant fusion proteins) or chemical means. Non-limiting examples of suitable chemical means include covalent bonding, disulfide bonding, hydrogen bonding, electrostatic bonding, and conformational bonding and may involve the use of homobifunctional or heterobifunctional cross linkers. Suitable cross-linking and conjugation methods are disclosed in Sen et al. (2001) *J. Hemato. Stem Cell Res.* 10:247-260; U.S. Pat. No. 6,642,363 and US Appl. No. 20060002852.

As used herein the terms "antibody" and "immunoglobulin" includes monoclonal and polyclonal antibodies and antigen binding fragments thereof. The term refers to a polypeptide or a functional fragment thereof that specifically bind to and recognizes an antigen. The antibody is encoded by an immunoglobulin gene, or can be derived from a polypeptide encoded by immunoglobulin gene that is modified for improved antigen binding or reduced immunogenicity. The antibody is comprised of at least one binding domain formed from the folding of variable domains of an antibody molecule to form three-dimensional binding spaces with an internal surface shape and charge distribution complementary to the features of an antigenic determinant of an antigen which allows an immunological reaction with the antigen.

The term "epitope" includes any antigenic determinant capable of specific binding to an immunoglobulin or antigen-binding fragment. The epitope is typically understood as the specific portion of the antigen that is involved in antigen-antibody binding. Epitopic determinants can consist of chemically active surface groupings of molecules such as exposed amino acids, aminosugars, or other carbohydrate side chains and often have specific three-dimensional structural characteristics, as well as specific charge characteristics. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The recognized immunoglobulin genes include variable region and constant region genes. The constant region genes include kappa, lambda, alpha, gamma, delta, epsilon, and mu. Immunoglobulin light chains are classified as either kappa or lambda. Immunoglobulin heavy chains are classified as gamma, mu, alpha, delta, or epsilon, which define the immunoglobulin classes, IgG, IgM, IgA, IgD and IgE, respectively.

An exemplary immunoglobulin (whole antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100-110 or more amino acids primarily responsible for antigen recognition.

Antibodies include naturally occurring as well as recombinant proteins comprising antigen specific binding domains, as well as antigen binding fragments thereof, including Fab, Fab', F(ab)$_2$, F(ab')$_2$ fragments, scFv, minibodies and nanobodies. The term "antigen-binding portion" or "antigen-binding fragment" of an antibody refers to one or more fragments of an antibody that retain the ability to specifically bind to an antigen. Antigen-binding portions may be produced by recombinant DNA techniques or by enzymatic or chemical cleavage of intact antibodies. Antigen-binding portions include Fab, Fab', F(ab')$_2$, Fv, and complementarity determining region (CDR) fragments, single-chain antibodies (scFv), chimeric antibodies, diabodies and polypeptides that contain at least a portion of an antibody that is sufficient to confer specific antigen binding to the polypeptide. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et. al. (1987) *J. Mol. Biol.* 196:901-917, and Chothia et al. (1989) *Nature* 342:878-883. An antibody or antigen-binding portion thereof can be derivatized or linked to another functional molecule (e.g., another peptide or protein). For example, an antibody or antigen-binding portion thereof can be functionally linked to one or more other molecular entities, such as another antibody (e.g., a bispecific antibody or a diabody), a detectable agent, a cytotoxic agent, a pharmaceutical agent, and/or a linking molecule.

The terms "autologous" and "homologous" refer to a sample deriving from or originating from the same subject. Autologous cells (e.g., cytotoxic immune cells), plasma or serum indicate that the biological composition is from the same individual as that to which the composition will be administered. For example, an autologous sample of cells can be obtained from an individual at birth, prior to pathogen infection, or just prior to treatment, and readministered to the same individual, e.g., after appropriate storage or processing. Autologous cells and samples are not expected to cause graft vs host disease, as they do not contain non-self antigens.

The term "allogeneic" refers to a sample deriving from or originating from a different individual. An allogeneic sample can be from a different individual that is genetically different, genetically similar (e.g., sibling). With reference to cells, plasma or serum, the term denotes that the individual from which the composition is obtained is non-identical to the composition will be administered. Allogeneic can also refer to samples generated from more than one non-identical individual (donor).

The terms "isogeneic" or "syngeneic" with reference to cells, plasma or serum, denote that the individual from which the biological composition is obtained is genetically identical or genetically similar to the individual to which the composition will be administered. Syngeneic can also refer to samples generated from more than one genetically identical or genetically similar individual (donor). Examples of syngeneic individuals can include identical twins.

A "control" sample or value refers to a sample that serves as a reference, usually a known reference, for comparison to a test sample. For example, a test sample can be taken from an individual with a suspected pathogen infection and compared to samples from a known infected individual or a known normal (non-infected) individual. A control can also represent an average value gathered from a population of similar individuals, e.g., infected patients or healthy individuals with a similar medical background, same age, weight, etc. A control value can also be obtained from the same individual, e.g., from an earlier-obtained sample, prior to disease, or prior to surgery (e.g., transplant). One of skill in the art will recognize that controls can be designed for assessment of any number of parameters. For example, a control can be devised to compare therapeutic benefit based on pharmacological data (e.g., half-life) or therapeutic measures (e.g., comparison of side effects or reduced viral titre). Controls can also be designed for in vitro applications, e.g., testing the activity of various bispecific antibodies and armed immune cell populations on cells expressing pathogenic antigens.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

II. BISPECIFIC BINDING MOLECULES

The bispecific binding molecules of the instant invention comprises a first antigen binding component that specifically binds to an antigen expressed on the surface of a cytotoxic immune cell (e.g. an activated T-cell) fused to a second antigen-binding molecule derived from a polyclonal population of antigen binding moieties that bind to an antigen of a pathogen expressed on the surface of an infected cell. One step in making a population of polyclonal bispecific binding molecules of the invention is identifying and selecting a first antigen binding molecule.

A. First Antigen Binding Moiety

A first antigen-binding moiety is any molecule that specifically binds to an antigen expressed on the surface of a cytotoxic immune cell (e.g., an activated T-cell), and can be fused to the second antigen binding moiety to generate a bispecific binding molecule. The first antigen binding moiety is specific for an antigen on a cytotoxic immune cell. Exemplary non-limiting cytotoxic immune cells that are bound by the first antigen binding moiety suitable for use with the instant invention may include T-cells, natural killer (NK) cells, dendritic cells, and macrophages. The first antigen binding molecule specifically binds to an antigen expressed on the surface of a cytotoxic immune cell. Exemplary non-limiting antigens expressed on the surface of the cytotoxic immune cells suitable for use with the invention may include CD2, CD3, CD4, CD5, CD8, CD11b, CD14, CD16a, CD45, CD56 and the Fc receptor. In a preferred embodiment the cytotoxic immune cell is a T-cell and the antigen is CD3.

Once the cytotoxic immune cell and the specific antigen are identified, a specific molecule can be selected for use as the first antigen binding moiety. Exemplary non-limiting molecules suitable for use as a first antigen binding moiety are well known in the art and may include: an antibody, an antibody fragment, a single chain variable fragment (scFv), and an antibody mimetic. These antigen-binding components suitable for use with the present invention can be either generated using methods well known in the art, or purchased from commercial suppliers (e.g., RDI Division of Fitzgerald Industries Intl (Acton Mass., USA) and eBioscience, (San Diego, Calif. USA), Santa Cruz Biotechnology (Santa Cruz, Calif. USA) and Abcam Intl (Cambrige, Mass. USA)). In some embodiments the binding moiety is an antibody. In some embodiments the antibody is modified, for example, to generate antibody fragments (e.g. Fab, F(ab')$_2$, scFv). In some embodiments, the binding moiety is a non-antibody molecule, such as an antibody mimetic, as described in more detail below. Non-limiting exemplary antibody mimetics suitable for use with the invention may include: anticalins, polypeptides with fibronectin type III domains, avimers, adnectins, and non-glycosylated single chain polypeptides having two or more binding domains.

1. Antibodies

Methods of producing monoclonal or polyclonal antibodies that react specifically with antigens expressed on the surface of a cytotoxic immune cell are well known to those of skill in the art. For example, preparation of monoclonal antibodies by immunizing mice with an appropriate immunogen is described in, e.g., Coligan, Current Protocols in Immunology (1991): Harlow & Lane, ANTIBODIES, A LABORATORY MANUAL, Cold Spring harbor Publication, New York (1988); Goding, Monoclonal Antibodies: Principles and Practice (2d ed. 1986); Kohler & Milstein, Nature 256:495497 (1975). Antibody preparation by selection of antibodies from libraries of nucleic acids encoding recombinant antibodies packaged in phage or similar vectors is described in, e.g., Huse, et al., Science 246:1275-1281 (1989) and Ward, et al., Nature 341:544-546 (1989). In addition, antibodies can be produced recombinantly using methods known in the art and described in e.g., Sambrook, et al., Molecular Cloning, A laboratory Manual (2nd ed. 1989); Kriegler, Gene Transfer and Expression: A Laboratory Manual (1990); and Current Protocols in Molecular Biology (Ausubel et al., eds., 1994).

The production of monoclonal antibodies is well known in the art. In general, spleen cells from an animal immunized with the desired immunogen (e.g., CD2, CD3, CD4, CD5, CD8, CD11b, CD14, CD16a, CD45, CD56, Fc receptor) are immortalized, commonly by fusion with a myeloma cell (see, Kohler & Milstein, Eur. J. Immunol. 6:511-519 (1976). Colonies arising from single immortalized cells are screened for the production of antibodies having the desired binding specificity and binding affinity for the particular antigen. In some embodiments, the immunized animal is a transgenic animal that expresses human immunoglobulin genes for the production of human antibodies, as disclosed in U.S. Pat. No. 6,833,268. In some embodiments, the production of human or humanized antibodies is carried out as described in U.S. Pat. No. 6,673,986, or using methods known to a person of ordinary skill in the art.

In some embodiments, the genes encoding the heavy and light chain immunoglobulins can be cloned from a hybridoma cell that produces a desired monoclonal antibody specific for a particular injury associated antigen. In some embodiments, gene libraries encoding heavy and light chains of monoclonal antibodies are generated. In some embodiments, random combinations of the heavy and light chain gene products are used to generate a pool of antibodies with differing antigenic specificities (see, e.g., Kuby, Immunology (3$^{rd}$ ed. 1997)). Nucleic acids encoding antibodies that specifically bind to an antigen expressed on the surface of a cytotoxic immune cell can be isolated directly from mRNA, cDNA, or DNA libraries using methods well known in the art, such as polymerase chain reaction (PCR) and ligase chain reaction (LCR) (see, e.g., U.S. Pat. Nos. 4,683,195 and 4,683,202; PCR Protocols: A Guide to Methods and Applications (Innis et al., eds, 1990)). Phage display technology can be used to identify antibodies and Fab fragments that specifically bind to selected antigens (see, e.g., McCafferty et al., Nature 348:552-554 (1990); Marks et al., Biotechnology 10:779-783 (1992)).

In addition to the antibodies generated using the methods well known in the art, or described herein, antibodies suitable for use as the first antigen binding moiety with the present invention can be purchased from commercial sources. For example, antibodies against CD2, CD3, CD4, CD5, CD8, CD11b, CD14, CD16a, CD45, CD56, Fc receptor and other antigens on the surface of cytotoxic immune cells can be purchased from commercial suppliers, for example RDI Division of Fitzgerald Industries Intl (Acton Mass., USA) and eBioscience, (San Diego, Calif. USA). These and other commercially available antibodies are suitable for use with the present invention.

2. Modification of Antibodies

Once an antibody of appropriate specificity and affinity has been obtained for use as the first antigen binding moiety, the antibody can be conjugated to the second antigen binding moiety, or the antibody can be modified prior to conjugation. Suitable modifications of the antibodies include, generation of antibody fragments, humanizing, primatizing, or chimerizing the antibody.

Antibody fragments suitable for use with the present invention include any antibody fragment capable of specifically binding to the particular antigen on the surface of the cytotoxic immune cell and wherein the fragment is capable of being fused to the second antigen binding moiety. Non-limiting exemplary antibody fragments may include: $F(ab')_2$, Fab, Fv, single chain Fv (scFv), dsFv, $V_L$ and $V_H$ (see, e.g., Fundamental Immunology (Paul ed., 4d ed. 1999); Bird, et al., *Science* 242:423 (1988); and Huston, et al., *Proc. Natl. Acad. Sci. USA* 85:5879 (1988)). The antibody fragments can be obtained by a variety of methods, including, digestion of an intact antibody with an enzyme, such as pepsin (to generate $(Fab')_2$ fragments) or papain (to generate Fab fragments); or de novo synthesis. Antibody fragments can also be synthesized using recombinant DNA methodology. In some embodiments $F(ab')_2$ fragments that specifically bind an antigen expressed on the surface of a cytotoxic immune cell are generated.

As mentioned above, humanized antibodies may be generated for use as a first antigen binding moiety. Humanized antibodies are antibodies in which the antigen binding loops, i.e., CDRs, obtained from the $V_H$ and $V_L$ regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., *Nature* 332:323-327 (1988); Marks et al., *Bio/Technology* 10:779-783 (1992); Morrison, *Nature* 368:812-13 (1994); Fishwild et al., *Nature Biotechnology* 14:845-51 (1996). Transgenic mice, or other organisms such as other mammals, may also be used to express humanized or human antibodies, as disclosed in U.S. Pat. No. 6,673,986.

3. Antibody Mimetics

In some embodiments, antibody mimetics are used as the first antigen binding moiety.

Antibody mimetics use non-immunoglobulin protein scaffolds as alternative protein frameworks for the variable regions of antibodies. As defined herein, antibody mimetics are polypeptides comprising one or more regions (i.e., loop regions) that are amenable to specific or random sequence variation such that the antibody mimetic specifically binds to an antigen of interest (e.g., an antigen expressed on the surface of a cytotoxic immune cell, such as CD2, CD3, CD4, CD5, CD8, CD11b, CD14, CD16a, CD45, CD56). Non-limiting exemplary antibody mimetics can include anticalins which are based on lipocalins and are described in Weiss and Lowman, *Chem Biol.*, 7(8):177-184 (2000); Skerra, *J. Biotechnol.* 74(4):257-275; and WO99/16873; polypeptides with a fibronectin type III domain and at least one randomized loop as described in e.g., WO01/64942 and U.S. Pat. No. 6,818,418; polypeptides with a β-sandwich structure as described in e.g. WO 00/60070; and non-glycosylated single chain polypeptides composed of two or more monomer domains, that can separately bind any type of target molecule including proteins, joined by a linker, as described in U.S. application Ser. Nos. 10/133,128 and 10/871,602.

The antibody mimetics having monomer domains of non-glycosylated single chain polypeptides described in U.S. application Ser. Nos. 10/133,128 and 10/871,602 are distinct from the complementarity-determining region (CDR) of an antibody. The antibody mimetic polypeptides are able to fold independently, form stable structures, and are heat stable unlike an antibody. For example, the polypeptides are stable to 95° C. for at least 10 minutes without an appreciable loss in binding affinity. Additional characteristics of the monomer domains includes low immunogenicity, low toxicity, small size sufficient to penetrate skin or other tissues, and a range of in vivo half-life and stability.

Antibody mimetics may be generated against the antigen bound by the first antigen binding moiety as described herein. For example, an antibody that binds to an antigen on the surface of a cytotoxic immune cell can be analyzed using methods known in the art, such as three-dimensional crystal structure analysis of the antibody-antigen interaction, to identify the specific residues that are critical for antigen binding. Once these residues have been identified, the loop regions of the antibody mimetics can be subjected to site directed mutagenesis such that the loop forms a binding pocket for the first antigen binding moiety Such modifications are described in, e.g., Vogt and Skerra, *Chembiochem.* 5(2):191-9 (2004).

Lipovsek et al. (U.S. Pat. Nos. 6,818,418 and 7,115,396) discloses an antibody mimetic featuring a fibronectin or fibronectin-like scaffold and at least one variable loop. Known as Adnectins, these fibronectin-based antibody mimetics exhibit many of the same desirable characteristics of natural or engineered antibodies, including high affinity and specificity for a targeted ligand. Further, these fibronectin-based antibody mimetics exhibit certain benefits over antibodies and antibody fragments. For example, these antibody mimetics do not rely on disulfide bonds for native folding and stability, and are therefore stable under conditions that would normally breakdown antibodies.

Beste et al. (*Proc. Natl. Acad. Sci. U.S.A.* (1999) 96(5): 1898-1903) discloses an antibody mimetic based on a lipocalin scaffold (ANTICALIN™). Lipocalins are composed of a β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that ANTICALIN™ would be suitable for use as an alternative to an antibody. ANTICALIN™ are small single chain polypeptides, typically between 160 and 180 residues in length, which provides several advantages over antibodies, including decreased cost of production, increased stability during storage, and decreased immunological reaction.

Hamilton et al. (U.S. Pat. No. 5,770,380) discloses a synthetic antibody mimetic using the rigid, non-peptide organic scaffold of calixarene, attached with multiple variable peptide loops as binding sites. The peptide loops all project from the same side geometrically from the calixarene, with respect to each other. Because of this geometric confirmation, all of the loops are available for binding, thereby increasing the binding affinity to the ligand. In comparison, however, to the other antibody mimetics, the calixarene-based antibody mimetic does not consist exclusively of polypeptide, and is therefore less susceptible to attack by protease enzymes, is relatively stable in extreme environmental conditions and has a long life-span. Further, due to the relatively small size of the antibody mimetic, it is less likely to produce an immunogenic response.

Murali et al. (*Cell. Mol. Biol.* (2003) 49(2):209-216) discloses a methodology for reducing antibodies into smaller peptidomimetics, termed "antibody-like binding peptidomimetics" (ABiP) which may also be used as an alternative to antibodies with the present invention.

Silverman et al. (*Nat. Biotechnol.* (2005) 23:1556-1561) discloses fusion proteins that are single chain polypeptides comprising multiple domains, termed "avimers." Developed from human extracellular receptor domains by in vitro exon shuffling and phage display, the avimers are a class of binding proteins somewhat similar to antibodies in their affinities and specificities for target molecules. These resulting multi-domain proteins may exhibit improved affinity (sub-nanomolar in some cases) and specificity compared to single epitope binding proteins. Additional details concerning the construction and use of avimers can be found in U.S. Pat. Pub. Nos: 20040175756, 20050048512, 20050053973, 20050089932, and 20050221384.

In addition to non-immunoglobulin protein frameworks, antibody properties have also been mimicked in compounds comprising RNA molecules and unnatural oligomers (e.g., protease inhibitors, benzodiazepines, purine derivatives and bb-turn mimics) all of which are suitable for use with the present invention as a first antigen binding moiety.

B. Second Antigen Binding Moiety

A second antigen-binding moiety is a member of a polyclonal population of binding moieties against the pathogen. Exemplary non-limiting pathogens that can be targeted with the compositions of the invention may include parasitic, bacterial, fungal, and viral pathogens.

Exemplary non-limiting sources for the polyclonal population of second antigen binding moieties include plasma and immunoglobulin enriched fractions of plasma, e.g., IVIG. Such plasma blood products can either be prepared from one or more allogeneic donors, from an autologous donor, from a syngeneic (isogeneic) donor, or purchased from commercial sources. Exemplary commercial sources of blood plasma products suitable for use as second antigen binding moieties include CYTOGAM (CSL Berhring, King of Prussia, Pa. USA), Talecris Biotherapeutics (Melville, N.Y. USA), Baxter Biopharmaceutical Solutions (Bloomington, Ind. USA) and Innovative Research (Novi, Mich. USA). Methods for preparing immunoglobulin enriched fractions from plasma are well known in the art, for example, U.S. Pat. Nos. 4,276,283; 6,504,012; and 7,125,552. Methods for preparing pathogen specific immune fractions are also well known in the art, for example, U.S. Pat. No. 4,174,388 discloses methods for preparing immunoglobulin enriched fractions for hepatitis B virus.

1. Donor Sources

In some embodiments the plasma or serum used for generating the second antigen binding moieties of the invention can be from an autologous source. In some embodiments the plasma or serum used for generating the second antigen binding moieties of the present invention can be from a single allogeneic source. In some embodiments the plasma or serum used for generating the second antigen binding moieties of the present invention can be from a pool of allogeneic donors. In some embodiments, the plasma or serum used for generating the second antigen binding moieties of the present invention can be a homologous mixture of autologous and allogeneic plasma or sera.

2. Commercially Available immunoglobulins:

a) CYTOGAM

The second antigen binding moieties can be derived from commercially available sources of blood plasma products. In some embodiments CYTOGAM (CSL Berhring, King of Prussia, Pa. USA) can be used as the source for the second antigen binding moiety. CYTOGAM (Cytomegalovirus Immune Globulin Intravenous (Human) (CMV-IGIV)) is a polyclonal antibody preparation generated from a large plasma pool obtained from normal individuals that is prepared as an intravenous preparation of an immunoglobulin G (IgG). The commercially available preparation contains a standardized amount of polyclonal antibody to cytomegalovirus (CMV). CYTOGAM is indicated for the prophylaxis of a variety of CMV disease states associated with the allogeneic transplantation of stem cells or organs, for example, kidney, lung, liver, pancreas and heart.

b) Hyperimmune Globulin Therapy

Talecris Biotherapeutics produces several concentrated immunoglobulins produced from human plasma which are also commercially available. These products include formulations for treatment of Hepatitis B (HyperHEP B® S/D; Hepatitis B Immune Globulin (Human)) and hepatitis A (GamaSTAN® S/D, Immune Globulin (Human)). In some embodiments of the present invention, HyperHEP B® S/D and/or GamaSTAN® S/D can be employed as the source for the second antibody binding moiety.

HyperHEP B™ S/D is prepared by cold ethanol fractionation from the plasma of donors with high titers of antibody to the hepatitis B surface antigen (anti-HBs). The immune globulin is isolated from solubilized Cohn fraction II. HyperHEP B™ S/D is formulated as a 15-18% protein solution at a pH of 6.4-7.2 in 0.21-0.32 M glycine. This commercially available formulation is suitable for use in the methods of the present invention for deriving the second antigen binding moiety.

GamaSTAN™ S/D treated with solvent/detergent is a sterile solution of immune globulin for intramuscular administration; it contains no preservative. GamaSTAN™ S/D is formulated as a 15-18% protein solution at a pH of 6.4-7.2 in 0.21-0.32 M glycine. The pH is adjusted with sodium carbonate. This commercially available formulation is suitable for use in the methods of the present invention for deriving the second antigen binding moiety.

c) Immunoglobulins

Baxter Biopharmaceutical Solutions (Bloomington, Ind. USA) also produces immunoglobulins, including IVIG (intravenous immune globulin) which is made from donated human source plasma. Several different formulations of IVIG are available and can be employed for various patient treatment methods. Examples of IVIG formulations include GAMMAGARD LIQUID [Immune Globulin Intravenous (Human)] 5%-10%, which is a specially formulated 10 percent IVIG therapy made from human plasma. Further, these commercially available formulations are suitable for use in the methods of the present invention for deriving the second antigen binding moiety.

Normal human plasma can be obtained from Baxter AG (NHP, Baxter, AG), as well as Innovative Research. Human plasma can be obtained as single donor or pooled formulations. Innovative Research provides both normal and disease state plasmas. Disease state plasmas commercially available include CMV positive plasma (Cytomegalovirus (CMV) Plasma), as well as Hepatitis B and Epstein-Barr virus positive plasma (Innovative Research). These and other commercially available human plasma formulations can be employed with the methods of the present invention for generating the second antigen binding moieties.

3. Methods for Preparing Plasma as a Source for the Second Antigen Binding Moiety The second antigen binding moieties of the present invention can also be derived from plasma obtained directly from infected individuals and the methods of collection of human plasma are well know and disclosed in the art. Methods for obtaining plasma, storing plasma, filtering plasma for viruses, and other plasma isolation and preparation techniques are well known in the art. See, e.g., U.S. Pat. No. 6,669,905 and U.S. Pat. No. 5,578,028. Plasma can be obtained from a single individual infected with the pathogen or can be pooled from multiple individuals infected with a pathogen or immunized for or vaccinated against viral and/or fungal pathogens. Pathogens can include viral and/or fungal pathogens, including but not limited to cytomegalovirus (CMV), hepatitis A virus (HAV), hepatitis virus type B (HBV), hepatitis virus type C (HCV), Epstein-Barr virus (EBV), herpes simplex virus (HSV), human immunodeficiency virus (HIV), human papilloma virus (HPV), *Pneumocystis carinii*, or *Aspergillus*. See, e.g., Zhong and Khanna, *Expert Reviews*, 5(3):449-459 (2007); Elliott S L, et al., *Journal of Virology*, 82(3):1448-57 (2008); Kim, et al., *Infectious Disease Clinics of North America* 21(1):201-17 (2007); U.S. Pat. Pub. No. 2008/0085286; Wells, et al., *Infection and Immunity*, 74(4):2446-2448 (2006).

In order to obtain the second antigen binding moieties for use in the present invention, plasma or sera must be screened for high titre antibodies that bind to the antigen of interest. It is further useful to screen for plasma or sera that contain high titres of antibodies for providing the polyclonal antibodies for use in obtaining the second antigen binding moieties.

Methods for determining antibody titre are well known in the art. Exemplary non-limiting methods for determining antibody titre suitable for use with the present invention include enzyme immunoassays, radioimmunoassays, magnetic immunoassays, lateral flow assays or fluorescence immunoassays. Examples of enzyme assays include but are not limited to indirect, sandwich, competitive and reverse ELISAs (enzyme-linked immunosorbent assays). ELISA plate are commercially available from several sources, including Affinity Life Sciences, Inc. (Milford, N.H.), which also provides customizable Mircoplates. Such Mircoplates can be customized to be specific for the target of interest.

4. Methods for Gamma Globulin Preparation

The second antigen binding moiety can also be derived from gamma globulin (γ-globulin) preparations. Gamma globulin preparations are derived from blood plasma products via a variety of techniques well known to those skilled in the art. Gamma globulin fractions of pooled plasma contain antibodies to many infectious agents and can be effective in the clinical management of a wide variety of disease states. Non-limiting exemplary methods for preparation and isolation of gamma globulin include Cohn fractionation, PEG fractionation, cationic exchange, anionic exchange, filtration, diafiltration, ultrafiltration, and precipitation. These and other methods well known to persons of skill in the art are suitable for use in the purification and isolation of gamma globulins from plasma for use in the invention.

U.S. Pat. No. 6,504,012 to Mamidi, et al., discloses methods for producing an intravenously-administrable gamma globulin solutions free of envelope and non-envelope viruses. The method involves performing Cohn fractionation of human plasma (Oncley, et al., *The Separation of the Antibodies, Isoagglutinins, Prothrombin, Plasminogen and β1-Lipo-protein into Subfractions of Human Plasma*. J. Am. Chem. Soc., 71:541 (1949)), followed by multiple PEG fractionation procedures, and subsequently followed by multiple virus inactivation steps. The starting material contemplated by the methods of Mamidi, et al., can include impurities, such as for example human blood-group antibodies, plasminogen, plasmin, kallikrein, prekallikrein activator, IgM, IgA, IgG polymers (including aggregates).

Mamidi, et al., further discloses that selected Cohn fractions containing immunoglobulins, for example fractions II+III or fractions I+II+III, may be further subjected to PEG (polyethylene glycol) fractionation procedures (see, for example, U.S. Pat. Nos. 4,876,088 and 4,845,199). Generally, at the first stage of PEG fractionation, PEG concentration and pH are optimized so that the selected antibody moieties remain in solution, while undesired proteins, impurities, and aggregates can be precipitated out of solution and removed by centrifugation. During the second stage of PEG fractionation, the concentration of PEG is increased and pH adjusted to precipitate the desired antibody moieties. Mamidi, et al., next discloses a two step viral inactivation, wherein the first step is selected from heat treatment, solvent or solvent-detergent. The second viral inactivation step is selected from heat treatment, solvent or solvent-detergent, but is not the same as the first viral step.

U.S. Pat. No. 4,093,606 to Coval, et al., discloses methods for producing an intravenously-administrable gamma globulin solution obtainable from Cohn Fraction II or Fraction II+III. The methods disclosed in Coval, et al., describe a process where the paste from Cohn Fraction II or Fraction II+III is dissolved in pyrogen-free water at a pH of 4.8 to 6.5. The water-insoluble material can then be separated and the filtrate subjected to fractional precipitations with polyethylene glycol (PEG) at successive wt./vol. concentrations of 4%, 5% and 12%. The last fractional precipitation can be performed at a pH of about 8.0. As described by Coval, et al., the first two fractional precipitations remove impurities and the final precipitation yields the desired gamma globulin.

U.S. Pat. No. 4,276,283 to Eibl, et al., discloses methods for producing an intravenously-administrable gamma globulin solutions free undesired protein impurities by a single or repeated precipitation with PEG. The methods of Eibl, et al., disclose the use of a three-step purification procedure. During the first purification step the immune-globulin-containing fraction is subjected to a treatment with an ammonium sulfate (AMS) solution having a content of 145 to 208 g/L (25 to 35% AMS-saturation) and a pH of 5.9 to 6.5. The precipitate is separated and the immune globulin is then precipitated from the remaining solution by treatment with an ammonium sulfate solution having a content of 268 to 289 g/L (44 to 47% AMS-saturation) at a pH of 8.0. The precipitate is then recovered, dissolved in water and the ammonium sulfate removed from the solution, for example by dialysis. During the second purification step, the remaining immune-globulin-containing solution is treated with PEG at a pH of 5.8 to 6.4 in the presence of a saccharide, polysaccharide or polysaccharide hydrolysate and with an ionic strength of at least 0.15. During the third purification step, the remaining immune-globulin-containing solution is subjected to a further treatment with polyethylene glycol at a pH of 6.4 to 7.0, whereupon the newly formed precipitate is separated and the immune globulin in the remaining solution, is precipitated at a pH of 7.0 to 7.5 by a polymeric precipitation agent.

After purification of the immune globulins by the methods disclosed in Eibl, et al., the immune globulins can be recovered from the solution, for example, by precipitation with water-soluble polymers. Examples of water soluble polymers include but are not limited to copolymers of ethylene oxide and polyoxypropylene 40 (BASF "PLURONIC"), dextrane, polyvinyl alcohol, polyvinyl pyrrolidone and polyethylene glycol (PEG).

U.S. Pat. No. 7,125,552 to Levy, et al., discloses methods of purification of immune globulins from blood plasma, in particular from Cohn Fractions I+II+III or II+III using a glycine extraction method. The Cohn Fraction is suspended in 19% ethanol and 81% water at a temperature of −4° C. to about −6° C. The majority of phospholipids are precipitated from immune globulin suspension by adjusting the pH of the suspension to 5.7 to 5.8 using sodium acetate and incubating at −4° C. to about −6° C. Glycine to a final concentration of 0.8 M and alcohol to a final concentration of 15% alcohol are added. The pH is adjusted to 5.2 to 5.4 using sodium acetate, and the temperature raised to −2° C. to about −3° C. and the precipitate separated using filtration or centrifugation.

The filtrate or centrifugate is the concentrated by ultrafiltration using a 100,000 molecular weight cut-off ultrafilter membrane. To reduce the glycine and alcohol content of the concentrate, solvent-exchange can be performed. Next, the protein solution is passed through an anion exchange chromatography column for removal of impurities (such as, IgA, IgM, albumin and other protein impurities). After elution from the column, viral inactivation is performed. In some embodiments, viral inactivation can be performed using the solvent-detergent method disclosed in U.S. Pat. No. 4,481,189. Following inactivation, the solvent-detergent mixture is removed from the protein solution by adsorption onto a C-18 resin and the solution then used in the methods of the present invention for generating a second antigen binding moiety.

U.S. Pat. No. 7,186,410 to Chtourou, et al., describes the preparation of human immunoglobulin concentrates for therapeutic use from human plasma or a fraction of human plasma. The methods of Chtourou, et al., allow for obtaining immunoglobulin G (IgG), immunoglobulins A (IgA) and immunoglobulins M (IgM). The process includes pre-purification through precipitation of lipid and proteic contaminants and single anion exchange chromatography step carried out at an alkaline pH, which allows for adsorption of the immunoglobulins on the anion exchange chromatographic material.

Pre-purification is carried out by any means known in the art of precipitating agents including but not limited to octanoic acid, tricalcium phosphate or bentonite. After the pre-purification step and prior to chromatography, a viral inactivation step, for example, using solvent-detergent inactivation is carried out. Other suitable viral inactivation methods suitable for use with the invention are well known in the art.

After viral inactivation, the pre-purified filtrate and solvent-detergent mixture is adjusted to a pH of 8.9 to 9.1 and subjected to chromatographic separation using, for example, a DEAE, TMAE or QAE groups-grafted gel of cross-linked polysaccharide or vinyl polymer. The immunoglobulins are adsorbed onto the column matrix and the non-adsorbed proteins flow through into the effluent. The immunoglobulins are then eluted with a suitable buffer, for example, a phosphate buffer at a pH between 4 and 7, and in some embodiments, at a pH of 6.2, to elute the IgG. The elution of a fraction containing the IgAs and IgG4s can also be carried out using the same phosphate buffer to which has been added 100 to 175 mM NaCl, at a pH of 6.0 to 6.3. The process can be continued by further elution with the same buffer adjusted to a pH of 6 to 7 to which has been added 250 to 350 mM NaCl to elute the IgMs.

The eluted immunoglobulins can be concentrated by ultrafiltration and then subjected to conventional sterile filtration, and then to filtration through nanometric filters of a porosity decreasing from 100 to 15 nanometers. This nanofiltration procedure enables viruses resistant to the solvent-detergent treatment to be eliminated. Methods of nanofiltration of viruses are well known in the art and any such methods can be employed (see, e.g., Burnouf and Radosevich, et al., *Nanofiltration of plasma-derived biopharmaceutical products*, Haemophilia, 9(1):24-37 (2003).)

The methods described above for preparation of immunoglobulins can be employed in the methods of the present invention for preparation of a second antigen binding moiety derived from plasma obtained from pathogen infected persons, or persons immunized with a pathogen.

Any of the methods described for preparation of immunoglobulin fractions or purified immunoglobulins are suitable for use in the preparation of the second antigen binding moiety of the present invention.

5. Depletion of HLA Antibodies

In some embodiments of the invention where the second antigen binding moieties are derived from allogeneic plasma sources, the plasma can be treated to deplete the blood product of antibodies that recognize HLA antigens.

Barnardo, et al., EP 1 873 526, describes methods of depleting major histocompatibility complex (MHC) antibodies, in particular human leukocyte antigen (HLA) reactive antibodies. The described methods use recombinant MHC or MHC-type (HLA or HLA-type) monomers capable of binding to MHC (HLA) antibodies in order to detect/deplete anti-MHC (anti-HLA) antibodies from a sample. Further, a number of HLA or HLA-type polypeptides are known in the literature and can be utilized with the methods of Barnardo, et al., for depletion of HLA antibodies. In some embodiments of the methods of Barnardo, et al., the MHC or HLA capturing molecules are linked to a solid support.

The HLA molecules can be attached to the solid support by any convenient means, as well as any method well known in the art, these can include for example but are not limited to attachment through hydroxyl, carboxyl, aldehyde or amine groups which may be provided by treating the solid support to provide suitable surface coatings. Attachment of the molecule to a solid phase can allow for the separation of the anti-HLA antibodies from the rest of the components in the sample.

Additional methods for removing anti-HLA antibodies from allogeneic plasma sources are well known in the art, for example, as described by Sivasai, et al., (2000) *Clin. Exp. Immunol.* 119:559-565, which discloses methods for the purification of anti-HLA antibodies from CYTOGAM. Briefly, the CYTOGAM is passed through an affinity column bound by anti-HLA antibodies such as W6/32, PA2'6, and MB40 (ATCC cell lines). The column is then washed with 50 mM Tris-HCl, pH 7.2 with 0.5 M NaCl. The unbound fraction containing the anti-idiotypic antibodies is collected and can be used to derive the second antigen binding moieties of the invention.

6. Phage Display

A population of heterogeneous antibodies directed to one or more pathogen antigenic molecules can be produced from a phage display library. Polyclonal antibodies can be obtained by affinity screening of a phage display library having a sufficiently large and diverse population of specificities with an antigen or antigens of interest. Examples of methods and reagents particularly amenable for use in generating and screening an antibody display library can be found in, for example, U.S. Pat. Nos. 5,223,409 and 5,514,548; PCT Publication No. WO92/18619; PCT Publication No. WO 91/17271; PCT Publication No. WO 92/20791; PCT Publication No. WO92/15679; PCT Publication No. WO 93/01288; PCT Publication No. WO 92/01047; PCT Publication No. WO 92/09690; PCT Publication No. WO 90/02809. A phage display library permits selection of a desired antibody or antibodies from a very large population of specificities. An additional advantage of a phage display library is that the nucleic acids encoding the selected antibodies can be obtained conveniently, thereby facilitating subsequent construction of expression vectors.

In some embodiments, the polyclonal population of antibodies directed to one or more antigenic molecules of a pathogen is produced from a phage display library according to Den, et al., 1999, *J. Immuno. Meth.* 222:45-57; Sharon et al. *Comb. Chern. High Throughput Screen.* 2000 3: 185-96; and Baecher Allan, et al., *Comb. Chem. High Throughput Screen.* 2000 2:319-325. The phage display library is screened to select a polyclonal sublibrary having binding specificities directed to the antigenic molecule or antigenic molecules of interests by affinity chromatography (McCafferty, et al., 1990, *Nature* 248:552; Breitling, et al., 1991, *Gene* 104:147; and Hawkins, et al., 1992, 1. *Mol. Biol.* 226:889). The nucleic acids encoding the heavy and light chain variable regions are then linked head to head to generate a library of bidirectional phage display vectors. The bidirectional phage display vectors are then transferred in mass to bidirectional mammalian expression vectors (Sarantopoulos, et al., 1994, *J. Immunol.* 152:5344) which are used to transfect a suitable hybridoma cell line. The transfected hybridoma cells are induced to produce the antibodies using any method known in the art.

In some embodiments, the population of antibodies directed to the one or more antigenic molecules of the pathogen is produced by a method using the whole collection of selected displayed antibodies without clonal isolation of individual members as described in U.S. Pat. No. 6,057,098. Polyclonal antibodies are obtained by affinity screening of a phage display library having a sufficiently large repertoire of specificities with, e.g., an antigenic molecule having multiple epitopes, preferably after enrichment of displayed library members that display multiple antibodies. The nucleic acids encoding the selected display antibodies are excised and amplified using suitable PCR primers. The nucleic acids can be purified by gel electrophoresis such that the full length nucleic acids are isolated. Each of the nucleic acids is then inserted into a suitable expression vector such that a population of expression vectors having different inserts is obtained. The population of expression vectors is then expressed in a suitable host.

7. Human Polyclonal Antibodies Obtained from Expression in Non-Human Animals

The invention of Maeda, et al., disclosed in US Publication No. 2004/0131620, describes preparation of human polyclonal antibody compositions having an antibacterial and/or antiviral activity. Maeda, et al., describes the use of a transgenic non-human for generating a human polyclonal antibody to a bacteria or virus. The transgenic non-human animal disclosed in the methods of Maeda, et al., contains a human antibody gene locus. Once generated, the transgenic animal is then infected with the pathogen of interest, plasma and/or serum obtained from infected non-human transgenic animal, and human polyclonal antibody isolated. Further, the antibody titer of human polyclonal antibody obtained by the methods of Maeda, et al., exceeds that of human pool plasma and can have a titer of 1 to 14 times more that human pool plasma. The methods of Maeda et al. are suitable for use in making a polyclonal population of second antigen binding moieties for use in the present invention.

C. Fusing the First Antigen Binding Moiety and the Second Antigen Binding Moiety In making the bispecific binding moiety of the instant invention, the first antigen binding component and the second antigen binding component are operably linked or fused. Methods for operably linking the antigen binding components to generate the bispecific binding molecule can include recombinant and chemical methods well known in the art.

Chemical conjugation techniques suitable for use with the present invention are well known in the art, and are described for example, in Sen et al. (2001) *J. Hemato. Stem Cell Res.* 10:247-260, and U.S. Pat. App. No. 20060002852. Chemical group conjugation typically involves the presence of a functional chemical group on both the first antigen binding moiety and the second antigen binding moiety. Exemplary functional groups include carboxylic acids, aldehydes, amines, sulfhydrals, and hydroxyl groups. The functional groups may be conjugated by direct crosslinking using homo- or hetero-bifunctional crosslinkers. A crosslinker suitable for use with the present invention is any crosslinker that couples the first and second antigen binding moieties via a chemical modification. Non-limiting exemplary cross-linkers suitable for use in the present invention include CDI, EDC, and glutaraldehyde.

In some embodiments, the functional groups on the first and second antigen binding moieties are identical, and may be conjugated in a one-step chemical cross-linking procedure using a homobifunctional linker. Exemplary homobifunctional cross-linkers may include amine reactive cross-linkers; amine reactive cross-linkers with PEO/PEG spacers; 1,5-difluoro-2,4-dinitrobenzene (DFDNB) (useful for cross-linking between small spatial distances); sulfhydral reactive linkers (maleimides react with —SH groups at pH 6.5-7.5, forming stable thioether linkages); and sulfhydral reactive linkers with PEO/PEG spacers. In some embodiments, heterobifunctional cross-linkers will be used to join two or more different functional groups allowing for sequential conjugations with specific functional groups of proteins while minimizing undesirable polymerization or self-conjugation.

In some embodiments, the conjugation method involves the activation of hydroxyl groups, on either the first or second antigen binding moiety with the agent carbonyldi-imidazole (CDI) in aprotic solvents (e.g., DMSO, acetone, or THF). Activation with CDI forms an imidazoyl carbamate complex with the hydroxyl group, which may then be displaced by binding the free amino group on the second component. The reaction is an N-nucleophilic substitution, which results in a stable N-alkylcarbamate linkage of the first and second antigen binding moieties. The coupling is optimal in the pH range of 9-10 and normally requires at least 24 hours. The resulting linkage is stable and resists hydrolysis for extended periods of time.

In some embodiments, the coupling method involves the use of 1-ethyl-3-(3-dimethylaminopropyl) carbodiimide hydrochloride (EDC) or "water soluble CDI" in conjunction with N-hydroxylsulfosuccinimide (sulfo NHS) to couple the exposed carboxyl group of one component to free amino groups present on the second component in a totally aqueous environment at a physiological pH of 7.0. Briefly, the EDC and sulfo-NHS in the reaction increases the efficiency of the EDC coupling by a factor of ten-fold and provides for exceptionally gentle conditions that ensure the viability of the resultant bispecific binding molecule.

Using either of the above protocols (CDI or EDC) it is possible to fuse the first and second antigen binding components containing a carboxyl or hydroxyl group in a suitable solvent system to prepare a bispecific binding molecule that retains it's antigen binding capabilities.

In some embodiments, coupling between the first and second antigen binding moiety is of a direct or indirect covalent nature. For example, the coupling may be through a linker bound to one component, or alternatively through an interaction between two molecules such as streptavidin and biotin. The coupling interaction may also be an electrostatic attraction. For example, the interaction between the first and second antigen binding moiety may be mediated by a positively charged molecule, such as polyethyleneimine or poly-lysine, present on one component and a negatively charged molecule present on the other component. In some embodiments, the first and second antigen binding moiety may be conjugated to each other by means of UV cross-linking In a preferred embodiment, as shown in FIG. 1, the first antigen binding moiety is cross-linked to Traut's Reagent with the polyclonal population of second antigen binding moieties is cross-linked to Sulpho-SMCC, as detailed in Sen M., et al., *J. Hemato. Stem Cell Res.* 10:247-260 (2001).

D. Population of Polyclonal Bispecific Binding Molecules

Binding the first antigen binding moiety to the second antigen binding moiety results in a heterogeneous population of polyclonal bispecific binding molecules, wherein the first antigen binding moiety of each molecule binds to the same antigen expressed on the surface of a cytotoxic immune cell (e.g., CD3 on an activated T-cell), and the second antigen binding moiety binds to an antigen of a pathogen expressed on a cell infected with the pathogen. The population of bispecific binding molecules is heterogeneous with respect to the second binding moiety, wherein at least two f the second antigen binding moieties of the population bind to two different antigens, or two distinct epitopes of an antigen, or bind to an antigen with different affinities.

In some embodiments, the population of polyclonal bispecific binding molecules will comprise at least 2, 3, 4, 5, 6, 7, 8, 9 10, 25, 50, 100 or more different heterogeneous antigen binding moieties.

In some embodiments, the population of bispecific binding molecules will bind to at least two different epitopes on an antigen expressed on the surface of a cell infected with the pathogen. In some embodiments, the population of bispecific binding molecules comprises at least two different bispecific binding molecules that bind an antigen of the pathogen with different affinities.

III. METHOD TREATING A PATIENT INFECTED WITH A PATHOGEN

The compositions of the invention can be used in a method to treat patients infected with a pathogen by arming activated cytotoxic immune cells with the bispecific binding moieties of the invention. The armed cytotoxic immune cells when administered to a patient will target and eliminate cell infected with the pathogen. Exemplary non-limiting cytotoxic immune cells that are suitable for arming with the bispecific binding molecules of the invention for treating a patient infected with a pathogen include activated T-cells (ATC), natural killer (NK) cells, dendritic cells, and macrophages. Non-limiting exemplary pathogen infections that can be treated with the compositions of the invention include viral, bacterial, fungal and parasitic pathogens.

In some embodiments, the pathogen is a virus. Exemplary non-limiting viral infections that can be treated with the polyclonal population of bispecific binding moieties of the invention include Cytomegalovirus (CMV), Epstein-Barr virus (EBV), Herpes simplex virus type I (HSV-1), Herpes simplex virus type II (HSV-II), BK virus (BKV), Hepatitis A (HSV-A), Hepatitis B (HSV-B), Hepatitis C (HSV-C), influenza, varicella, adenovirus, rinderpest, rhinovirus, echovirus, rotavirus, respiratory syncytial virus, papilloma virus, papova virus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picornaviridae, enteroviruses, caliciviridae, any of the Norwalk group of viruses, togaviruses, such as Dengue virus, alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, human herpesvirus-6, cercopithecine herpes virus 1 (B virus), and poxviruses.

Bacterial diseases or disorders that can be treated or prevented by the use of polyclonal population of bispecific binding molecules of the invention include, but are not limited to, those caused by Mycobacteria rickettsia, Mycoplasma, *Neisseria* spp. (e.g., *Neisseria menigitis* and *Neisseria gonorrhoeae*), *Legionella, Vibrio cholerae,* Streptococci, such as *Streptococcus pneumoniae, Corynebacteria diphtheriae, Clostridium tetani, Bordetella pertussis, Haemophilus* spp. (e.g., *influenzae*), *Chlamydia* spp., enterotoxigenic *Escherichia coli,* and *Bacillus anthracis* (anthrax).

Fungal diseases or disorders that can be treated or prevented by the use of the polyclonal population of bispecific binding molecules of the present invention include, but are not limited to, *Pneumocystis carinii* or *aspergillus.*

Protozoal diseases or disorders that can be treated or prevented by the use of the polyclonal population of bispecific binding molecules of the present invention include, but are not limited to, *plasmodia, eimeria, Leishmania,* and *trypanosoma.*

A. Isolating Cytotoxic Immune Cells

One step in treating a patient infected with a pathogen according to the invention requires isolating cytotoxic immune cells. In some embodiments, the cytotoxic immune cells are isolated from a blood sample comprising peripheral blood mononuclear cells (PBMC) that can be armed with the polyclonal population of bispecific binding molecules of the invention. In some embodiments, the blood sample is obtained from an autologous donor. In some embodiments the blood sample is obtained from a syngeneic donor. In still other embodiments the blood sample is obtained from an allogeneic donor or pool of allogeneic donors. In some embodiments where the blood sample is obtained from an allogeneic donor or a pool of allogeneic donors the cells are treated, either prior to or after the cell separation and isolation step, with pre-irradiation or mitomycin-c to inactivate the cells to reduce the risk of graft versus host disease.

Once the blood sample is obtained the cytotoxic immune cells to be armed with the compositions of the invention are isolated. Methods for separating and isolating a particular cell type from PBMCs are well known in the art. Suitable methods of cell isolation include density gradient centrifugation using a PERCOLL™ gradient or Ficoll-Hypaque (Lymphoprep from Nycomed Pharma, Oslo, Norway). Cells can be further purified or subpopulations of cells can be selected using positive/negative selection techniques well known in the art, for example using negative magnetic immunoadherence which utilizes a cocktail of monoclonal antibodies directed to cell surface markers present on the cells negatively selected. Depending on the choice of antibody the desired cells can be positively selected using this method. In some embodiments, fluorescence activated cell sorting (FACS) is used to isolate a desired cell population. Additional methods for cell separation and isolation will be well known to persons of skill in the art. In some embodiments the isolated cytotoxic immune cells are washed, and cryopreserved in suitable media for future use.

In some embodiments, the cytotoxic immune cell may need to be activated (e.g., T-cells) and expanded ex-vivo prior to arming with the bispecific binding molecules of the invention. Methods for activating and expanding cytotoxic immune cells ex-vivo are well known in the art. A method for activating T-cells suitable for use with the instant invention is described below.

B. Activating T-Cells

In some embodiments, isolated T-cells are activated by stimulation with a soluble or immobilized anti-CD3 antibody ex vivo as described in U.S. Pat. No. 6,352,694; and U.S. Pat. Pub. No. 2003/0185823. The isolated cells are then expanded ex vivo by culture with low doses of IL-2 or IL-7 and IL-15, in the absence of exogenous growth factors or accessory cells. See, U.S. Pat. Pub. No. 2003/0185823.

The T-cells can be activated by contacting ex vivo with soluble anti-CD3 antibodies (about 10-20 ng/ml) or anti-CD3 antibodies immobilized on a solid/insoluble support (1-5 µg/ml). In some embodiments, the anti-CD3 antibody is OKT3 (muromonab-CD3) available from Ortho-Biotech (Raritan, N.J.), or monoclonal antibody G19-4 available from Bristol-Meyers Squibb. Additional antibodies suitable for use with the invention to activate T-cells ex vivo are well known by persons of skill in the art.

In some embodiments, activation is carried out by co-stimulation of the T-cells with anti-CD3 antibody and anti-CD28 antibody. An anti-CD28 antibody suitable for use with the invention is Murm 9.3 (Abbott-Biotech). Additional anti-CD28 antibodies suitable for use with the invention will be well known to persons of skill in the art and can be purchased form numerous commercial sources including RDI Division of Fitzgerald Industries Intl. (Acton Mass. USA) and eBioscience (San Diego Calif. USA). In some embodiments, the T-cells are activated using co-stimulaton with an anti-CD3 antibody (e.g., OKT3) and an anti-CD28 antibody (e.g., Murm 9.3) co-immobilized on a solid support with a 1:1 stoichiometry.

After activation of the T-cells by stimulation with anti-CD3 or co-stimulation with anti-CD3 and anti-CD28, the cells are expanded in the presence of low doses of IL-2 (10 IU/ml to about 500 IU/ml) for about 14 days. In some embodiments, the cells are expanded in the presence of low doses of IL-7 (25-100 ng/ml), optionally in the presence of IL-15 (25-100 ng/ml). The cells can be expanded in any combination of IL-2, IL-7, and/or IL-15, as well as recombinant cytokines and non-naturally occurring recombinant cytokines that act to expand activated T cells. For example, IL-2 can be used alone, or in combination with IL-7 and/or IL-15. Similarly, IL-7 can be used alone, or in combination with IL-2 and/or IL-15. One of skill will understand that activated T cells can be expanded in a variety of conditions (see, e.g., Fernandez-Botran, *Advanced Methods in Cellular Immunology* (CRC Press 2000).

Recombinant IL-2 (PROLEUKIN IL-2) can be purchased from Chiron (Emeryville, Calif.). IL-7, and IL-15 can be purchased from ProSpec-Tany TechnoGene Ltd. (Rehovot Israel). Additional sources for interleukins suitable for use with the invention will be well known to persons of skill in the art. In some embodiments the activated and expanded T-cells are cryopreserved with 10% fetal bovine serum and 10% DMSO fin liquid nitrogen and then thawed as needed for arming with a population of bispecific binding molecules of the invention.

C. Arming the Activated Cytotoxic Immune Cells with a Population of the Polyclonal Bispecific Binding Molecules The compositions and methods as disclosed herein provide for a surprisingly effective treatment of patients infected with a pathogen due to the low concentration of the population of polyclonal bispecific binding molecules required to arm the cytotoxic immune cells to achieve a desired therapeutic effect. In addition, due to the polyclonal nature of the pathogen binding, the bispecific antibodies of the invention are able to target effector cells to infected cells despite immune evasion by the pathogen.

In some embodiments, the concentration of the population of polyclonal bispecific binding molecules needed to arm the activated cytotoxic immune cells is at least an order of magnitude less than other compositions in the art to achieve the same desired effect. In some embodiments, the cells are armed with between 0.001 ng and 50 ng of the population of bispecific binding molecules per $10^6$ cytotoxic immune cells. In some embodiments the cells are armed with between 0.01 and 5 ng of the population of bispecific binding molecules per $10^6$ cells. In some embodiments the cells are armed with between 0.1 and 1ng of the population of bispecific binding molecules per $10^6$ cells. In some embodiments the cells are armed with 1 ng of the population of bispecific binding molecules per $10^6$ cells. In some embodiments, the concentration of the population of polyclonal bispecific binding molecules used to arm the cytotoxic immune cells is 100 ng, 50 ng, 40 ng, 30 ng, 20 ng, 15 ng, 10 ng, 5 ng, 4 ng, 3 ng, 2 ng, 1 ng, 0.5 ng, 0.1 ng, 0.05 ng, 0.01 ng, 0.005 ng, and 0.001 ng per $10^6$ cytotoxic immune cells.

The arming of the cells can be carried out using any suitable means known in the art. In some embodiments, for example, the cells can be washed, and resuspended at a desired concentration and then incubated with a specific concentration of the population of polyclonal bispecific binding molecules. After a suitable incubation period to allow the bispecific binding molecules to bind to the cytotoxic immune cells (e.g., activated T-cells), the cells are washed to remove any unbound binding molecules. In some embodiments, the armed cytotoxic immune cells are stored in liquid nitrogen for future use. See, Uberti et al., *Clin. Immunol. and Immunopath.* (1994); Ueda et al. *Transplantation* (1993). In some embodiments the armed cytotoxic immune cells are resuspended in a suitable media at a desired concentration and administered to a patient in need thereof.

IV. PHARMACEUTICAL FORMULATIONS

The pharmaceutical formulations of the present invention can comprise a population of polyclonal bispecific binding molecules as described herein, or cytotoxic immune cells (e.g., activated T-cells) armed with a population of polyclonal bispecific binding molecules as described herein. Methods of formulating compositions as pharmaceutical formulations are well known in the art, for example as found in standard references as Remington's Pharmaceutical Sciences 18th ed. (1995) Mack Pub. Co. Easton, Pa.

In some embodiments, e.g., where the cytotoxic immune cells are obtained from an autologous source, it is advantageous to irradiate the cytotoxic immune cells prior to administration. This provides for a defined dose of effector cells that can target pathogen-infected cells without dividing further. The cytotoxic immune cells can be rendered unable to divide using other methods known in the art, e.g., mytomycin c. This can be helpful in avoiding GVHD, if necessary. The inventors have found, however, that the armed effector cells of the invention are unlikely to cause GVHD, regardless of allogenicity.

The pharmaceutical formulations of the invention can be administered to a patient alone, or in conjunction with other therapies suitable for treatment of the particular pathogen infection. For example, pharmaceutical formulations of the present invention can be administered in conjunction with antiviral or antifungal therapeutics related to the specific pathogen with which the individual is infected. In some embodiments, pharmaceutical formulations of the invention can be administered prior to, contemporaneous with or subsequent to administration of an antiviral or antifungal compound.

The pharmaceutical formulations of the present invention can be formulated for administration to a patient. Such pharmaceutical formulations can further comprise a pharmaceutically acceptable carrier. As used herein the language "pharmaceutically acceptable carrier" can include any solvents, dispersion media, coatings, antibacterial and antifungal agents, isotonic and absorption delaying agents, and the like, compatible with pharmaceutical administration of a population of polyclonal bispecific binding molecules of the invention or cytotoxic immune cells (e.g., activated T-cells) armed with a population of polyclonal bispecific binding molecules of the invention.

A pharmaceutical formulation of the invention is formulated to be compatible with its intended route of administration and can be administered by any suitable means known in the art. Examples of routes of administration suitable for use with the invention include intravenous, intraarterial, parenteral, intradermal, subcutaneous, transdermal (topical), intraperitoneal and transmucosal, intranasal, topical, vaginal, rectal, intrathecal and intraocular. The route of administration is typically intravenous or intraarterial.

Solutions or suspensions used for parenteral, intradermal, intramuscular, or subcutaneous application can include but are not limited to the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as but not limited to hydrochloric acid or sodium hydroxide. The preparation can be enclosed in ampoules, disposable syringes or multiple dose vials made of glass or plastic, as well as any other preparation suitable for use with the invention and well known to persons of skill in the art.

Pharmaceutical formulations suitable for injectable use include but are not limited to sterile aqueous solutions (where water soluble) or dispersions and sterile powders for the extemporaneous preparation of sterile injectable solutions or dispersions. In embodiments where the pharmaceutical formulation comprises immune cells, physiologic solutions that are isotonic are used. For intravenous administration, suitable carriers include but are not limited to physiological saline, bacteriostatic water, Cremophor EUM (BASF; Parsippany, N.J.) or phosphate buffered saline (PBS). In all cases, the pharmaceutical formulation must be sterile and should be fluid to the extent that the viscosity is low and formulation is injectable. It must be stable under the conditions of manufacture and storage and must be preserved against the contaminating action of microorganisms, such as bacteria and fungi. In some embodiments the bispecific binding molecules are stored at 4° C. until they break down, and are typically stable for years.

The carrier can be a solvent or dispersion medium containing, for example but not limited to, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants or by any other methods well known in the art. Prevention of the action of microorganisms can be achieved by various antibacterial and antifungal agents, for example but not limited to, parabens, chlorobutanol, phenol, ascorbic acid, thimerosal, and the like. In some embodiments, isotonic agents can be included, for example but not limited to, sugars, polyalcohols such as mannitol, sorbitol, sodium chloride in the formulation.

It is advantageous to formulate pharmaceutical formulations in dosage unit form for ease of administration and uniformity of dosage. The term "dosage unit form" as used herein refers to physically discrete units suited as unitary dosages for the subject to be treated; each unit containing a predetermined quantity of the pharmaceutical formulations of the present invention calculated to produce the desired therapeutic effect in association with the required pharmaceutical carrier. The specification for the dosage unit forms of the invention are dictated by and directly dependent on the unique characteristics of the pharmaceutical formulations and the particular therapeutic effect to be achieved, as well as the limitations inherent in the art of compounding such pharmaceutical formulations for the treatment of individuals. In some embodiments the armed immune cells are frozen in dosage specific aliquots.

The pharmaceutical formulations can be included in a kit, in a container, pack, or dispenser together with instructions for administration. In some embodiments, the population of bispecific binding molecules can be provided as a kit, and the cytotoxic immune cell could be activated and armed with the population of bispecific binding molecules presented in the kit. In some embodiments, the armed cytotoxic immune cells can be provided as a pre-frozen packaged aliquot that is thawed at the bedside and immediately infused into a patient in need thereof.

V. DOSING AND ADMINISTRATION

The bispecific binding molecules of the present invention can be administered to a patient in the form where such bispecific binding molecules are bound to activated cytotoxic immune cells (e.g., activated T-cells), as described herein. The bispecific binding molecules of the present invention can be bound to activated cytotoxic immune cells (e.g., activated T-cells) at extremely low concentrations as low as 0.001 ng per $10^6$ activated cytotoxic immune cells or lower. In some embodiments the activated cytotoxic immune cells are armed with a concentration of bispecific binding molecules in the range of 0.001 ng to 50 ng per $10^6$ cells or higher. In some embodiments, the activated cytotoxic immune cells are armed with a concentration of bispecific binding molecules in the range of 0.01 ng to 5 ng per $10^6$ cells. In some embodiments, the activated cytotoxic immune cells are armed with a concentration of bispecific binding molecules in the range of 0.1 ng to 1.0 ng per $10^6$ cells.

The activated cytotoxic immune cells once armed with bispecific binding molecules can be administered at a large range of concentrations, and there is no apparent dosing toxicity limit for activated T-cells up to 160 billion in 8 divided doses over 4 weeks (2 doses/week). In some embodiments, the total amount of cytotoxic immune cells (e.g. activated T-cells) armed with a population of polyclonal bispecific binding molecules of the invention administered to a patient in need thereof is in the range of $1\times10^8$ cells to $50\times10^{11}$ cells. In some embodiments, the amount of armed cytotoxic immune cells administered to a patient in need thereof is in the range of $1\times10^{10}$ cells to $5\times10^{10}$ cells. In some embodiments the total amount of armed cytotoxic immune cells administered to a patient in need thereof is about $1\times10^8$ cells, $1\times10^9$ cells, $5\times10^9$ cells, $1\times10^{10}$ cells, $5\times10^{10}$ cells, $15\times10^{10}$ cells, $25\times10^{10}$ cells, or $50\times10^{10}$ cells.

In some embodiments the pharmaceutical formulations of the present invention are administered as a single dose. In some embodiments the pharmaceutical formulations of the present invention are administered as multiple doses. In some embodiments, the pharmaceutical formulation is administered as a single cycle. In some embodiments, multiple cycles of a pharmaceutical formulation are administered. In some embodiments the pharmaceutical formulations of the present invention are administered as multiple doses over several days. In some embodiments the pharmaceutical formulations of the present invention are administered as multiple doses over several weeks. In some embodiments the pharmaceutical formulations of the present invention are administered as multiple doses over several weeks by weekly administration.

The total amount of armed cytotoxic immune cells to be administered to a patient in need thereof is determined by a variety of factors including but not limited to the dosage and frequency of administration as required and tolerated by the patient. The dosage and administration schedule can be tailored to provide sufficient quantity of the pharmaceutical formulations to effectively treat the patient. Determining exact dosage and administration schedules will depend on a variety of factors, and is well within the skill of medical professional treating the patient.

EXAMPLES

Example 1

Activated T-Cells Armed with Anti-CD3×
Anti-CMV Polyclonal Bispecific Antibody
(CMVBi) Target CMV Infected Fibroblast In Vitro This example demonstrates that in a CMV infected fibroblast tissue culture model, normal ATC armed with anti-CD3× anti-CMV(poly) selectively targeted and eliminated CMV-infected cells.

Introduction:

CMV reactivation and infection can cause profound negative outcome post allogeneic SCT. Presently available management strategies are not very effective and are associated with adverse effects. Induction of anti-CMV T-cell responses using vaccine strategy has not been helpful in immunocompromised hosts. Immunotherapy with CMV specific donor-derived cytotoxic T lymphocytes (CTL) is a proven strategy after allografting but it is dose-limiting, expensive, labor intensive, and difficult to replicate in most centers. Non-toxic targeted therapy is needed to improve clinical outcomes. Previously we have shown that ex vivo expanded anti-CD3 activated T cells (ATC) exhibit high levels of tumor-specific cytotoxicity when anti-CD3 is chemically heteroconjugated with anti-Her2/neu or anti-CD20 (see, Sen, M., et al. J. Human Stem Cell Res. 2001; Gall, J. M., et al. Exp. Hematol. 2005). Here we have demonstrated a novel strategy of using ATC armed ex-vivo with engineered CMVBi to target CMV antigens and have tested the strategy in an in vitro tissue culture model using CMV-infected fibroblasts with T cells from seropositive and seronegative normal human donors.

Materials and Methods:

ATCs were produced by anti-CD3 (OKT3) and interleukin 2 (IL-2) activation of peripheral blood mononuclear cells (PBMC) from normal donors. CMVBi was created by chemical heteroconjugation of OKT3 (murine IgG2a) monoclonal antibody and polyclonal anti-CMV (Cytogam®) (see, FIG. 1). Specific cytotoxicity directed at CMV-infected and non-infected targets by CMVBi armed ATC, ATC alone, Cytogam® alone, CMVBi alone, and CMVBi armed or unarmed PBMC was tested in a $^{51}$Cr labeled CMV infected or uninfected fibroblasts as target cells. Cytotoxicity was assessed with arming doses of CMVBi and irrelevant BiAb ranging from 1 to 500 ng/$10^6$ ATC with effector to target ratios (E:T) ranging from 25:1 to 3.125:1. Interferon gamma (IFNγ) EliSpots were done to determine cytokine response after exposing CMV-infected and uninfected fibroblasts to unarmed ATC and ATC armed with CMVBi.

Figure 2:
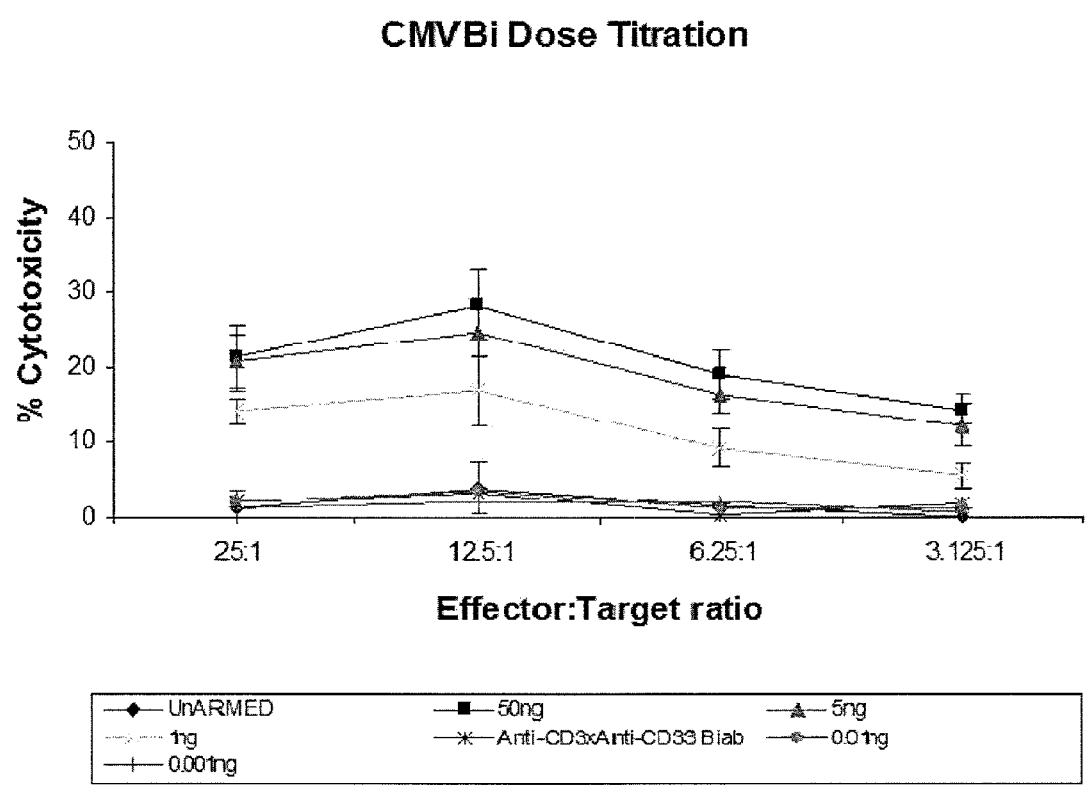
FIG. 2 shows a dose titration curve for a population of polyclonal bispecific binding molecules against CMV (CM-VBi). Specific cytotoxicity mediated by ATC armed with CMVBi plateaus at an arming dose of 50 ng/$10^6$ ATC on CMV infected MRCS targets at an effector:target ratio (E:T) ranging from 3.125:1 to 25:1. Anti-CD3× anti-CD33 was used as irrelevant control antibody.
Figure 3:
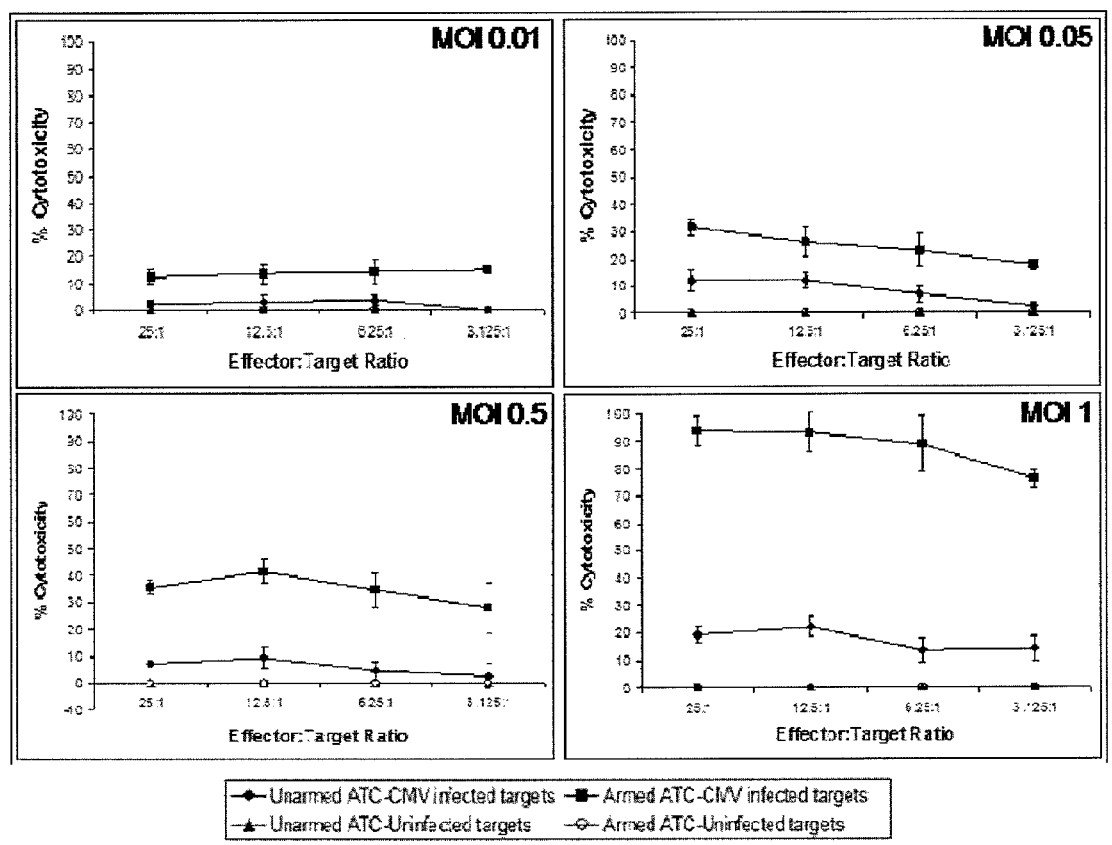
FIG. 3 shows specific incremental cytotoxicity mediated by ATC armed with CMVBi (50 ng/$10^6$ ATC) at effector:target ratios ranging from 3.125:1 to 25:1. The targets (MRCS) were infected with CMV.
Figure 4:
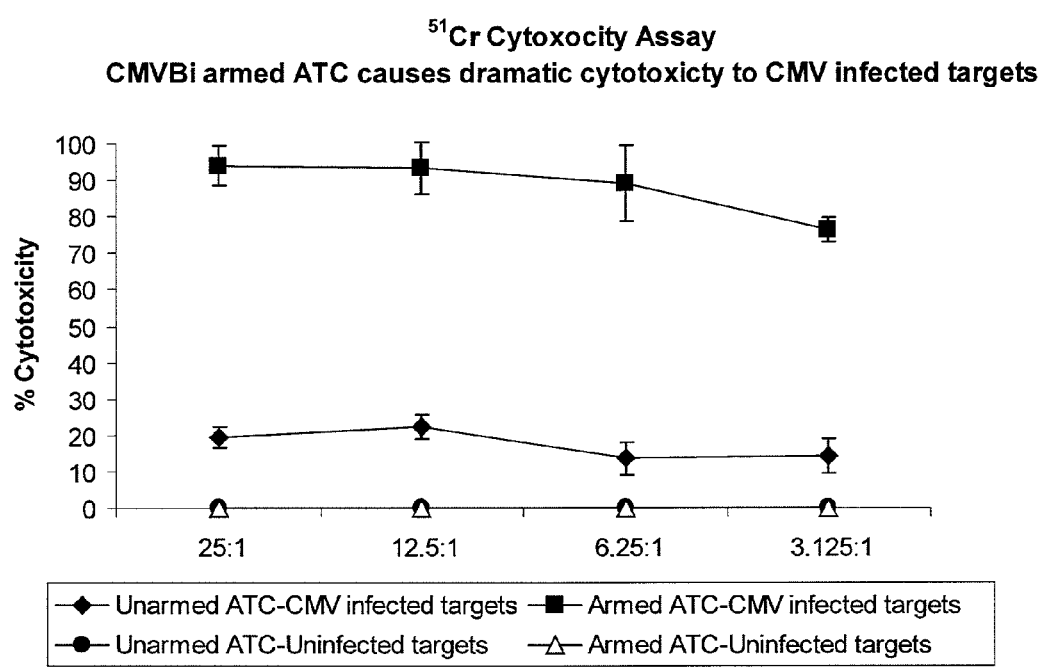
FIG. 4 shows markedly enhanced killing of CMV-infected targets at an MOI=1 with ATC armed with a dose of 50 ng CMVBi/$10^6$ compared to unarmed ATC. Mean [±SEM]% specific cytotoxicity was 89±2, 95±3, 86±2 and 71±3% for armed ATC and 24±4, 27±4, 20±4, and 18±2% for unarmed ATC at E:T ranging from 25:1 to 3.125:1.

Results:

Arming with CMVBi at as little as 1 ng/$10^6$ ATC resulted in cytotoxicity of target cells significantly above unarmed ATC (see, FIG. 2). There was an incremental increase in cytotoxicity with CMVBi armed ATC with a corresponding incremental increase in multiplicity of infection (MOI) of CMV in the target cells (see FIG. 3). At all E:T (25:1, 12.5:1, 6.25:1, and 3.125:1), ATC armed with a dose of 50 ng CMVBi/$10^6$ demonstrated markedly enhanced killing of CMV-infected targets at an MOI=1 compared to unarmed ATC. Mean [±SEM]% specific cytotoxicity was 89±2, 95±3, 86±2 and 71[±3% for armed ATC and 24±4, 27±4, 20±4, and 18±2% for unarmed ATC at E:T ranging from 25:1 to 3.125:1 (see, FIG. 4). In the uninfected control cells both unarmed and armed ATC caused lysis barely detectable over spontaneous lysis. Furthermore, ATC derived from seronegative donor could be armed and mediate high levels of cytotoxicity in this model and ATC have been shown to be non-responsive to alloantigens in mixed lymphocyte cultures (Lum, unpublished). Immunoflourescent studies showed that CMVBi armed ATC specifically aggregated around GFP fluorescent marked CMV infected fibroblasts whereas unarmed ATC did not have any specific aggregation. Cytokine secretion analyzed using IFNγ EliSpots confirmed the cytotoxic activity of the CMVBi armed ATC.

Conclusion:

Use of polyclonal Cytogam® to make CMVBi for arming effectively created polyclonal cytotoxic ATC which can bind and lyse CMV-infected cells expressing varying antigenic targets. Such surprising high levels of cytotoxicity on a per ng of CMVBi resutls from multiple CMV antigens are being targeted by multiple antibodies in the pooled sera acting additively or synergistically to enhance binding and cytotoxicity. This non-MHC restricted specific killing strategy is useful for the prevention and/or treatment of CMV infection after allogeneic SCT using donor-derived ATC.

Example 2

Activated T Cells Armed with Anti-CD3× Anti Hepatitis B Virus (HBV) Polyclonal Bispecific Antibody (HBVBi) Target HBV Antigen Expressing Cells In Vitro and Downregulate Viral Replication and Transcription In Vivo Introduction:

HBV causes noncytolytic liver infection in humans. Patients who clear the infection can develop a vigorous cellular immune response against multiple viral epitopes, which is associated with an acute necro-inflammatory liver disease (reviewed in Chisari and Ferrari *Annu Rev Immunol* 1995; 13:29-60). Over 400 million people worldwide are estimated to be persistently infected with HBV and (Lee WM. N Engl J Med 1997; 337:1733-1745) and a quarter of those are expected to die of hepatocellular carcinoma (HCC) (Lee et al. (1997) *N Engl J Med* 337:1733-1745; Beasley *Cancer* 1988; 61:1952-1956).

Vaccines directed against the hepatits B surface antigen (HBs) can bind all viral subtypes based on reactivity against the "a" region determinants. At least three epitopes have been identified in this region based on a competitive analysis of a panel of monoclonal antibodies (Waters et al. (1991) *Virus Research* 22:1-12). Antiviral therapy can also be used to control HBV viral load, which correlates with disease progression (Chen et al. *JAMA* 2006; 295:65-73). Standard treatments include interferon alpha and the nucleoside analogs (NA) lamivudine, adefovir, and entecavir (Sloan et al. *Antiviral Therapy* 2008; 13:439-447).

However, viral load is only reduced in approximately 20-40% of patients with interferon, while the use of NAs leads to resistance mutations, depending on the particular drug and use profile (Kao et al *J Hepatol* 2000; 33:998-1002; Sloan et al. *Antiviral Therapy* 2008; 13:439-447). Drug-resistant HBV mutations commonly occur in the polymerase gene, and can also occur in the HBV surface antigen due to the overlapping gene structure of the HBV genome. Thus, antiviral escape mutants can develop resistance to HBs neutralizing antibodies.

There is no cure for persistent HBV infection. Additional therapies are required to control viral replication, while also limiting the development of antiviral, antibody, and T cell resistance, in order to prevent progression to liver cirrhosis and HCC.

T cells can be used to reduce HBV replication and gene expression in a non-cytolytic manner via release of interferons alpha, beta and gamma and TNF alpha and/or through T cell cytotoxicity (Guidotti 1996 *Immunity*; McClary 2000 *J Virol*; Bertoni et al. *J Clin Invest* 1997; 100: 503-13; Rivero et at *J Viral Hepatitis* 2002; 9:107-113). Although liver disease is a major side effect of anti-HBV cytotoxicity, viral replication and transcription can be controlled via adoptive transfer of HBV-specific T cells with a limited degree of liver damage. Clinical studies have shown that cytokine-induced killer T cells can be administered to patients with primary hepatocellular carcinoma, and some clinical responses in chronic HBV patients to infusion of immune cells activated with anti-CD3, IL-2 and IFN-gamma (Shi et at *World J Gastroenterol* 2004; 10:1146-1151; Sun et al. *J. Clin Virol* 2006; 35: 26-32). Clinical feasibility of using expanded patient T cells is limited because many patients with chronic HBV have restricted T cell repertoires against the virus which may lack the required specificity to control the disease. Moreover, expansion of highly active T cell clones can be difficult, as with approaches for cancer treatment (Ferrari et al. *J Immunol* 1990; 145:3442-9; Chisari and Ferrari Annu Rev Immunol 1995; 13:29-60; Lohr et al. *J Infect Dis* 1993; 168(5): 1133-9; Knutson et al. C*ancer Immunol Immunother* 2006; 55:96-103).

The present invention overcomes these limitations by converting a large number of readily obtainable T cells into a highly active polyclonal population of anti-viral T cells with broad specificity.

Materials and Methods A: In Vitro Targeting of HBV Antigen-Expressing Cells.

Numerous cell types can be prepared that express one or more viral antigens. Non-limiting examples include: rat fibroblast cell lines (Gholson et al. Gastroenterology 1990; 98:968-975); and Epstein-Barr virus-immortalized B-cell lines (Guilhot et al. J Virol 1992; 66: 2670-2678).

ATC are produced and armed with BiAb as in Example 1 but with the use of polyclonal immunoglobulin against HBV, e.g., the FDA approved HepaGam (Cangene Biopharma), or a mixture of two or more monoclonal antibodies against cell surface expressed proteins of HBV-infected cells. A dose titration of BiAb-armed cells is added to the selected target cells expressing or not expressing (negative control) HBV antigens on the surface. The titration reflects an increasing effector:target ratio. Additional negative controls can include unarmed T cells, and HepaGam only. Levels of target cell killing are measured using a Cr-release assay (or other comparable cytotoxicity assay); the levels of cytokines released are measured in the cell supernatants by specific ELISAs or by cytokine-specific EliSpots.

Results A:

Increasing E:T ratios of BiAb-armed T cells show selective killing of HBV target cells vs. non-expressing control targets. The levels of anti-viral cytokines, including IFNa, IFNb, IFNg and TNFa are also elevated relative to negative control conditions.

Materials and Methods B: In Vivo Regulation of HBV Viral Replication and Transcription.

HBV transgenic mice (Guidotti *Immunity* 1996; 4: 25-36) are injected intravenously with increasing numbers of MHC-matched murine ATC armed with polyclonal anti-HBV× anti-murine CD3 BiAbs. Liver tissue is harvested on different days after cell administration and total RNA and DNA isolated. Northern and Southern blots are performed as in Guidotti (1996) to demonstrate a reduction in HBV genome transcription and replication, respectively.

Conclusion:

Use of polyclonal Hepagam, or combinations of different anti-HBV monoclonal antibodies, is effective at targeting HBV antigen-expressing cells. This non-MHC restricted, HBV-specific anti-viral activity is useful for the control of HBV infection in chronically infected patients and/or patients with hepatocellular carcinoma.

Example 3

Activated T Cells Armed with Anti-CD3× Anti-IVIG BiAb Target BK (BKV) and Herpes Simplex Viruses (HSV) Infected Fibroblasts In Vitro Introduction:

BKV and HSV infection and reactivation can cause profound negative outcomes in immunocompromised patients. BKV is associated with nephropathy in renal transplant patients, and hemorrhagic cystitis after bone marrow transplantation (Reploeg et al. *Clinical Infectious Diseases* 2000; 33:191-202). HSV types 1 and 2 commonly cause mucocutaneous lesions (Styczynski et al. *Bone Marrow Transplantation* 2009; 43:757-770).

Materials and Methods:

ATCs are produced as in Example 1. IVIG Bispecific antibody (IVIGBi) is created by chemical heteroconjugation of OKT3 (murine IgG2a) monoclonal antibody against CD3, and polyclonal IVIG. Several sources of IVIG are commercially available (e.g., Tegeline, LFB, France; Octagam, Octapharma, Australia; Gammagard, Baxter, and Endobulin, Immuno, Austria). A dose titration of IVIGBi is tested alongside standard controls on BK- or HSV-infected fibroblasts, as described in Example 1. An additional control/comparison can include an enriched polyclonal bispecific antibody against a different pathogen (e.g., CMVBi). Levels of target cell killing are measured using a Cr-release assay (or other comparable cytotoxicity assay); the levels of cytokines released are measured in the cell supernatants by specific ELISAs or by cytokine-specific EliSpots.

Results:

IVIG represents a sample of IgGs directed to many different antigens pooled from multiple individuals, thus, IVIG will include BK- and HSV-specific antibodies. A comparison of the relative killing of virally infected cells by CMVBi and IVIGBi determines the optimal components of the bispecific antibody for use with a particular viral target.

Conclusion:

Use of polyclonal IVIG or Cytogam to make an anti-CD3 conjugated BiAb for arming activated T cells is effective at lysing BK- or HSV-infected cells expressing varying antigenic targets.

Example 4

Activated T Cells Armed with Anti-CD3× Anti Hepatitis C Virus (HCV) Polyclonal Bispecific Antibodies (HCVBi) Target HBV Antigen Expressing Cells In Vitro Introduction:

HCV is major cause of hepatitis world wide, with approximately 170 million infected individuals. Most patients become chronic carriers and are at risk of developing cirrhosis and hepatocellular carcinoma. A strong, multispecific and long-lasting cellular immune response is thought to be necessary to resolve acute infections.

A subgroup of patients at great risk for reininfection are liver transplant recipients. A clinical trial involving polyclonal immunoglobulin against hepatitis surface antigen (HBIG) showed a reduction in HCV infection in transplant patients (Feray et al. *Ann Intern Med* 1998; 128: 810-816) indicating that the preparation of pooled anti-HBV serum also contains neutralizing antibodies agasint HCV. A pooled human sera (Civacir) enriched for anti-HCV antibodies for the prophylaxis of HCV reinfection following liver transplantation is also available. These two products can used to prepare BiAbs for arming ATC for treatment of chronic HCV infection.

Alternatively, a combination of known mAbs can be used. This approach includes (1) identifying HCV antigens accessible to armed ATC targeting, (2) preparing or obtaining mAbs against these antigens, e.g., via phage display, and if necessary (3) characterizing the combination of mAbs that provide the required level of activity, specificity and strain coverage for a given patient population. For example, the HCV E2 protein has been shown to be a target for antibody dependent cellular cytotoxicity (ADCC) using HCV patient sera and the E2 protein is expressed on transfected cells and at the sinusoidal pole of hepatocytes in chronic HCV (Nattermann et al. *Hepatology* 2005; 42: 499-504; Dumonceaux et al. *J Virol* 2003; 77:13418-13424; Verslype et al. *FEBS Lett* 2003; 546: 385-390; Verslype et al. *Hepatology* 2000; 32:213A).

Materials and Methods:

Multiple mAbs or the pooled human sera are conjugated with anti-CD3 to form HCVBi. The HCVBi is then used to arm ATC, which are tested for cell killing of HCV infected target cells expressing the E2 gene of different quasispecies. The HCVBi armed ATC are also tested for cell killing and cytokine release on fibroblast lines transfected with different HCV quasispecies.

Results:

Polyclonal HCVBi armed ATC are highly active and selective against HCV-infected, and HCV-transfected, cell lines.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention. Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

It is to be further understood that the Examples and embodiments described herein are for illustrative purposes only, and that various modifications or changes will be suggested to persons of ordinary skill in the art in light of the disclosures herein, and are to be included within the spirit and purview of this application and the scope of the appended claims. All publications, patents, and patent applications cited herein are hereby incorporated by reference in their entirety for all purposes.

What is claimed is:

1. A composition comprising a heterogeneous population of polyclonal bispecific binding molecules, where each bispecific binding molecule comprises a first and a second antigen binding moiety,
    wherein the first antigen binding moieties specifically bind to an antigen on the surface of a cytotoxic immune cell, said first antigen binding moieties being the same or different, and
    wherein the second antigen binding moieties are a heterogeneous polyclonal population of antigen binding moieties against multiple different epitopes on one or more pathogenic antigens expressed or presented on the surface of a cell infected with the pathogen, said antigens being the same or different,
    wherein the first antigen binding moiety is fused to the second antigen binding moiety to form the bispecific binding molecule.

2. The composition of claim 1, wherein the cytotoxic immune cell is selected from the group consisting of an activated T-cell, a natural killer (NK) cell, a dendritic cell, and a macrophage.

3. The composition of claim 1, wherein the first binding moiety and the second binding moiety are antibodies or antigen binding fragments thereof.

4. The composition of claim 3, wherein the first binding moiety is a monoclonal antibody or antigen binding fragment thereof and the second binding moiety comprises a population of polyclonal antibodies or an antigen binding fragments thereof.

5. The composition of claim 4, wherein the heterogeneous population of polyclonal bispecific binding molecules comprises at least two different antibodies as second antigen binding moieties with each antibody having different antigen recognition specificity and being directed to different epitopes on the pathogen.

6. The composition of claim 4, wherein the population of polyclonal antibodies is derived from an immunoglobulin (Ig) enriched serum fraction.

7. The composition of claim 6, wherein the Ig serum fraction is depleted of antibodies that recognize human leukocyte antigen (HLA) molecules.

8. The composition of claim 4, wherein the polyclonal antibody is derived from an autologous donor.

9. The composition of claim 4, wherein the polyclonal antibody is derived from an allogeneic donor, or a pool of allogeneic donors.

10. The composition of claim 1, wherein the cytotoxic immune cell is derived from an autologous donor.

11. The composition of claim 1, wherein the cytotoxic immune cell is derived from an allogeneic donor.

12. The composition of claim 1, wherein the first antigen binding moiety specifically binds to a molecule selected from the group consisting of CD2, CD3, CD4, CD5, CD8, CD11b, CD14, CD16a, CD28, CD45 and CD56.

13. The composition of claim 12, wherein the first antigen binding moiety is an anti-CD3 antibody, or functional equivalent, or antigen binding fragment thereof.

14. The composition of claim 13, wherein the anti-CD3 antibody is OKT3 or a functional equivalent.

15. The composition of claim 1, wherein the cytotoxic immune cell is armed with the population of polyclonal bispecific binding molecules.

16. The composition of claim 1, wherein the first antigen binding moiety specifically binds to an Fc receptor.

17. The composition of claim 15, wherein the arming dose of the population of polyclonal bispecific binding molecules is in the range of 0.001 ng to 50 ng per 106 cytotoxic immune cells.

18. The composition of claim 15, wherein the arming dose of the population of polyclonal bispecific binding molecules is in the range of 0.01 ng to 5 ng per 106 cytotoxic immune cells.

19. The composition of claim 15, wherein the arming dose of the population of polyclonal bispecific binding molecules is in the range of 0.1 ng to 1.0 ng per 106 cytotoxic immune cells.

20. The composition of claim 1, wherein the pathogen is an infectious agent.

21. The composition of claim 20, wherein the infectious agent is selected from the group consisting of a virus, a bacterium, a fungus, and a parasite.

22. The composition of claim 21, wherein the pathogen is a virus.

23. The composition of claim 22, wherein the virus is selected from the group consisting of cytomegalovirus (CMV), hepatitis A virus (HAV), hepatitis virus type B (HBV), hepatitis virus type C (HCV), Epstein-Barr virus (EBV), BK virus (BKV), herpes simplex virus (HSV), human immunodeficiency virus (HIV), and human papilloma virus (HPV).

24. The composition of claim 23, wherein the virus is CMV.

25. The composition of claim 21, wherein the population of second antigen binding moieties is derived from an IVIG preparation.

26. The composition of claim 25, wherein the IVIG preparation is CYTOGAM.

27. The composition of claim 21, wherein the pathogen is a fungus.

28. The composition of claim 27, wherein the fungus is *Pneumocystis carinii* or *aspergillus*.

* * * * *